United States Patent
Takahashi

(10) Patent No.: US 7,554,572 B2
(45) Date of Patent: Jun. 30, 2009

(54) IMAGE PICKUP APPARATUS FOR CAPTURING SPECTRAL IMAGES OF AN OBJECT AND OBSERVATION SYSTEM INCLUDING THE SAME

(75) Inventor: Susumu Takahashi, Iruma (JP)

(73) Assignee: Olympus Corporation, Tokyo (JP)

( * ) Notice: Subject to any disclaimer, the term of this patent is extended or adjusted under 35 U.S.C. 154(b) by 731 days.

(21) Appl. No.: 11/135,391

(22) Filed: May 24, 2005

(65) Prior Publication Data
US 2005/0264672 A1   Dec. 1, 2005

(30) Foreign Application Priority Data
May 25, 2004   (JP)   ............... 2004-154659

(51) Int. Cl.
*H04N 7/18*   (2006.01)
*H04N 5/225*   (2006.01)

(52) U.S. Cl. .................. 348/65; 348/335; 600/476; 356/303

(58) Field of Classification Search .............. 348/45, 348/65, 72
See application file for complete search history.

(56) References Cited

U.S. PATENT DOCUMENTS

| | | | |
|---|---|---|---|
| 5,078,150 A | | 1/1992 | Hara et al. |
| 5,112,125 A | * | 5/1992 | Neumann ............. 356/73 |
| 5,782,770 A | | 7/1998 | Mooradian et al. |
| 5,828,451 A | * | 10/1998 | Bellus et al. ............. 356/326 |
| 5,905,571 A | * | 5/1999 | Butler et al. ............. 356/328 |
| 6,118,127 A | * | 9/2000 | Liu et al. ............. 250/458.1 |
| 7,009,916 B2 | * | 3/2006 | Kyong et al. ............. 369/44.23 |
| 2002/0167665 A1 | * | 11/2002 | Yeung et al. ............. 356/344 |

FOREIGN PATENT DOCUMENTS

JP   2802061   7/1998

* cited by examiner

*Primary Examiner*—Sinh N Tran
*Assistant Examiner*—Hung H Lam
(74) *Attorney, Agent, or Firm*—Arnold International; Bruce Y. Arnold

(57) ABSTRACT

An image pickup apparatus has a construction in which a diffraction element is provided in an observation optical system. Zero-order light that is transmitted straight through the diffraction element and one of the +1st-order diffracted light and the −1st-order diffracted light that is diffracted by the diffraction element are imaged onto an image pickup surface of an image pickup apparatus. The imaging areas of the zero-order light and one of the +1st-order diffracted light and the −1st-order diffracted light that is diffracted by the diffraction element do not overlap on the image pickup surface of the image pickup apparatus. With this construction, a small image pickup apparatus that provides a high-resolution spectral image and a color image of an object can be obtained.

5 Claims, 18 Drawing Sheets

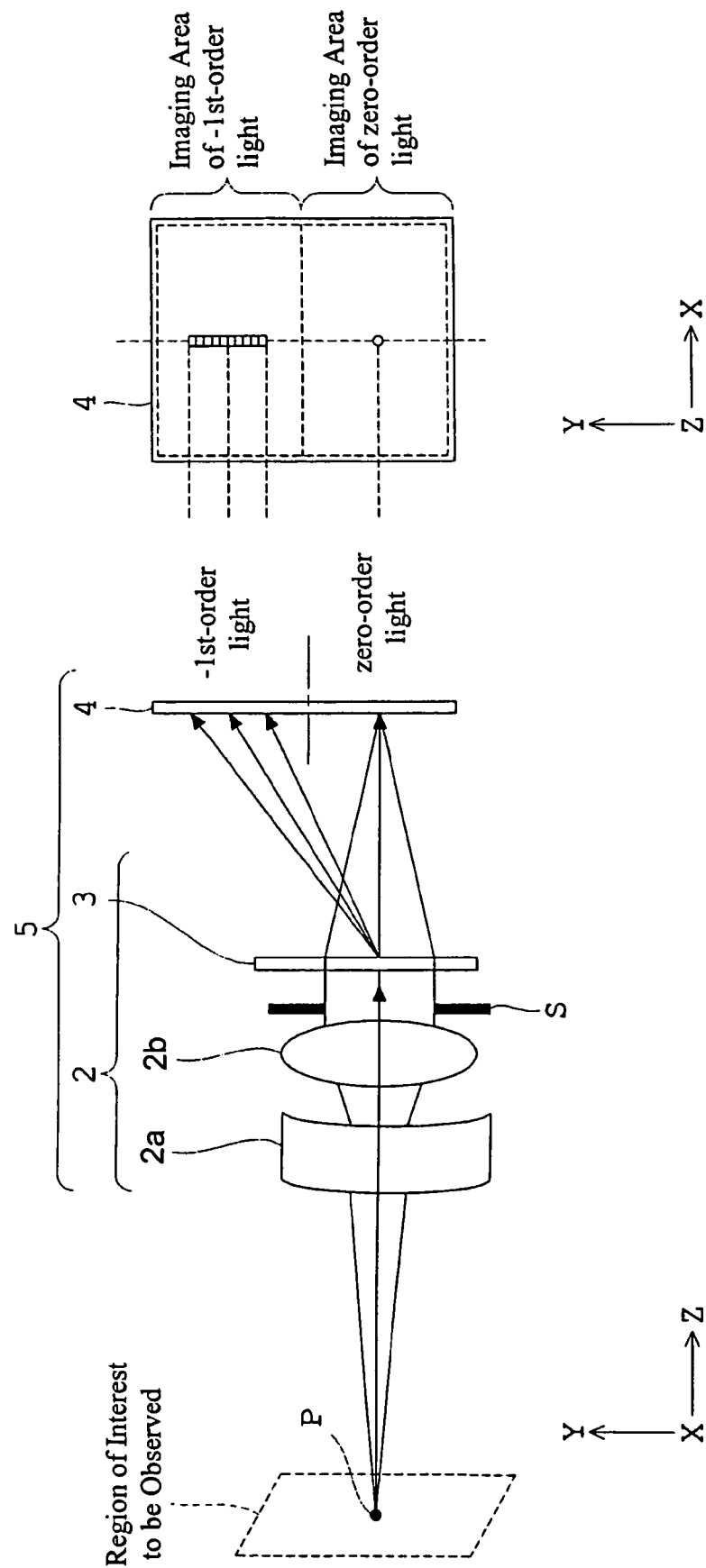

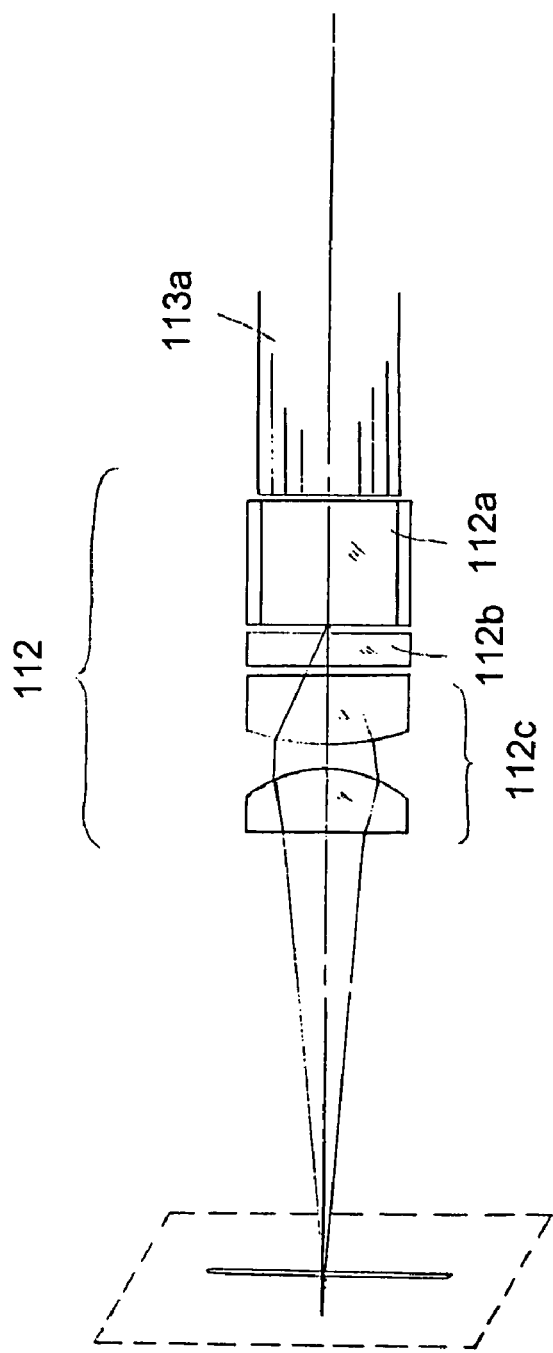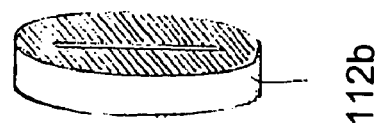
Fig. 6(a)
Fig. 6(b)

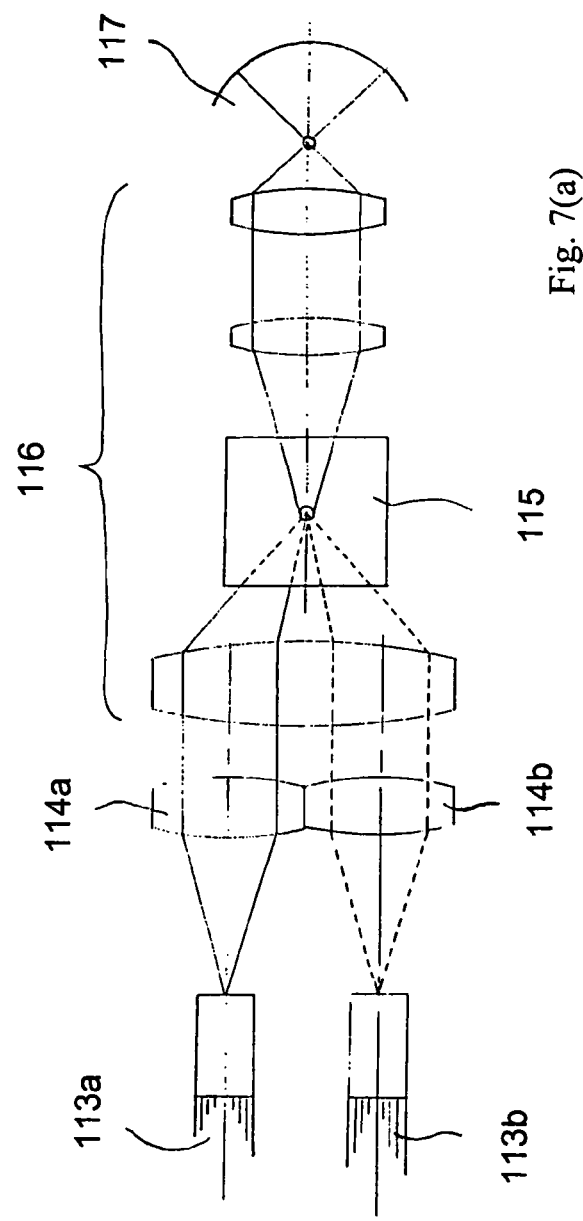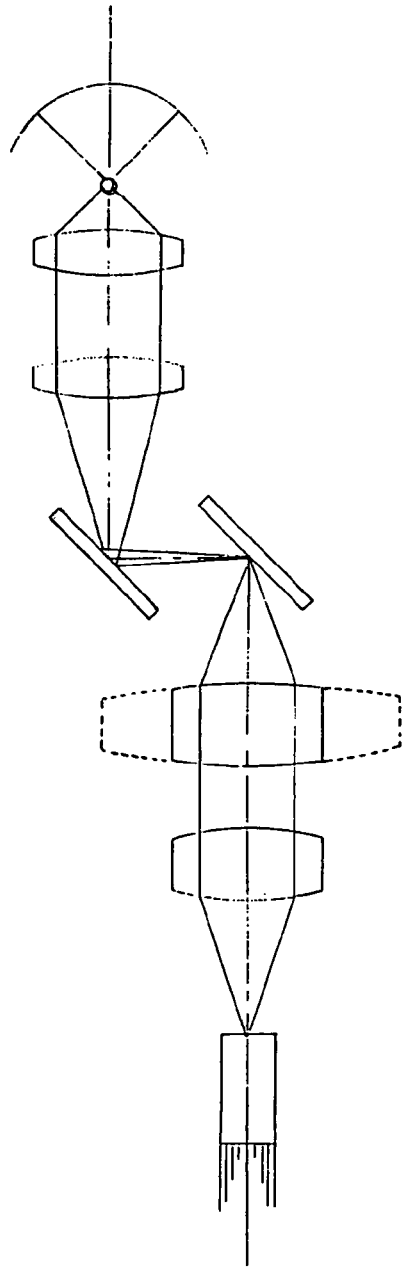

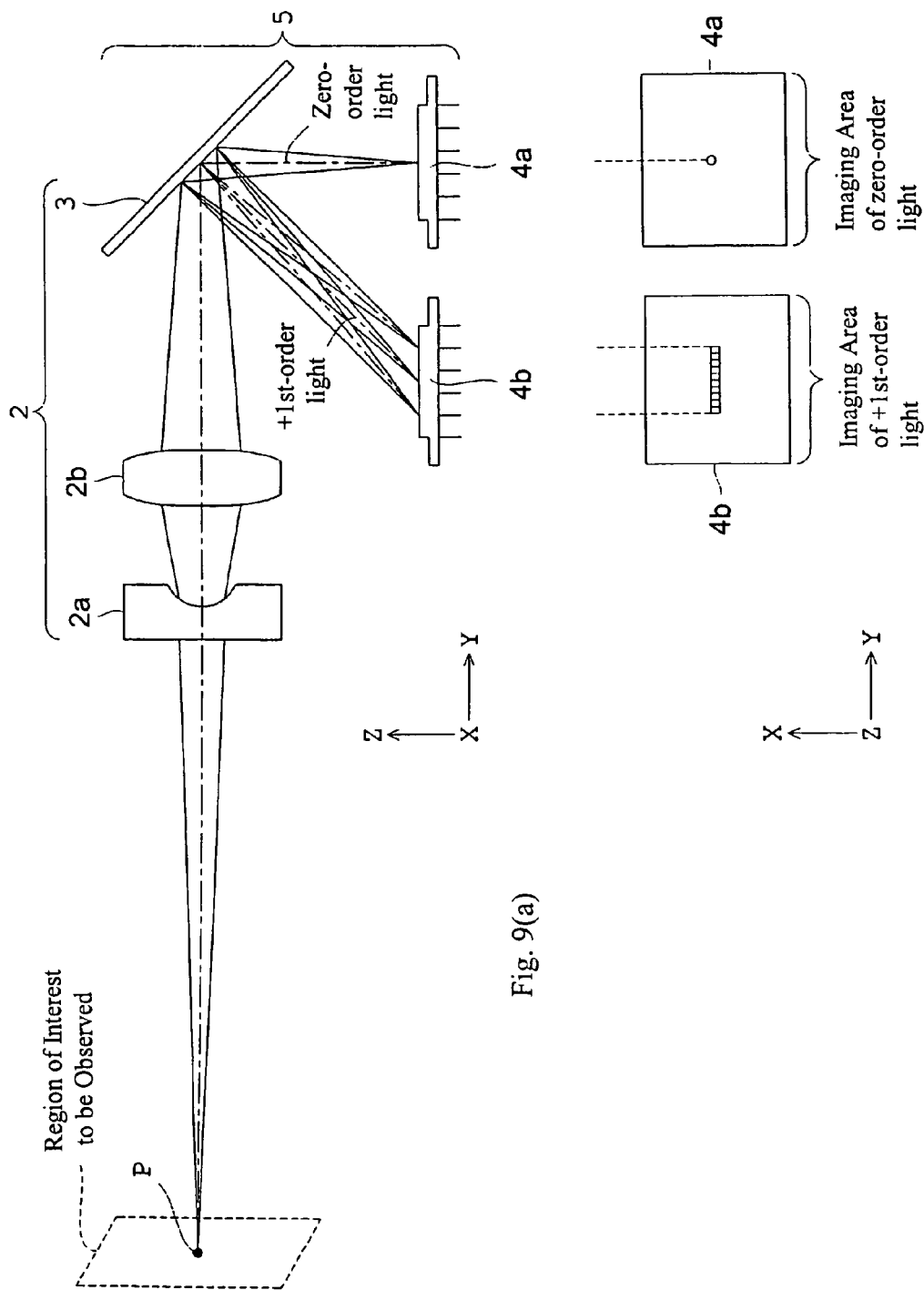

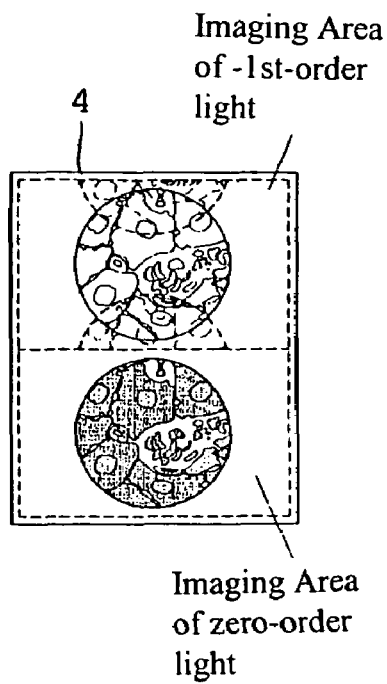
Imaging Area of -1st-order light
Imaging Area of zero-order light
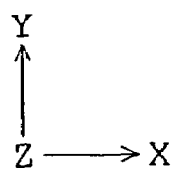
Fig. 10(b)
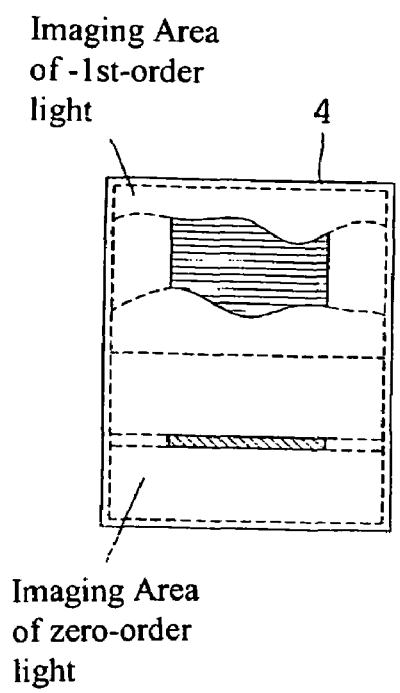
Imaging Area of -1st-order light
Imaging Area of zero-order light
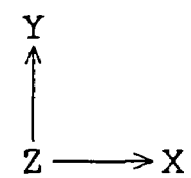
Fig. 10(c)

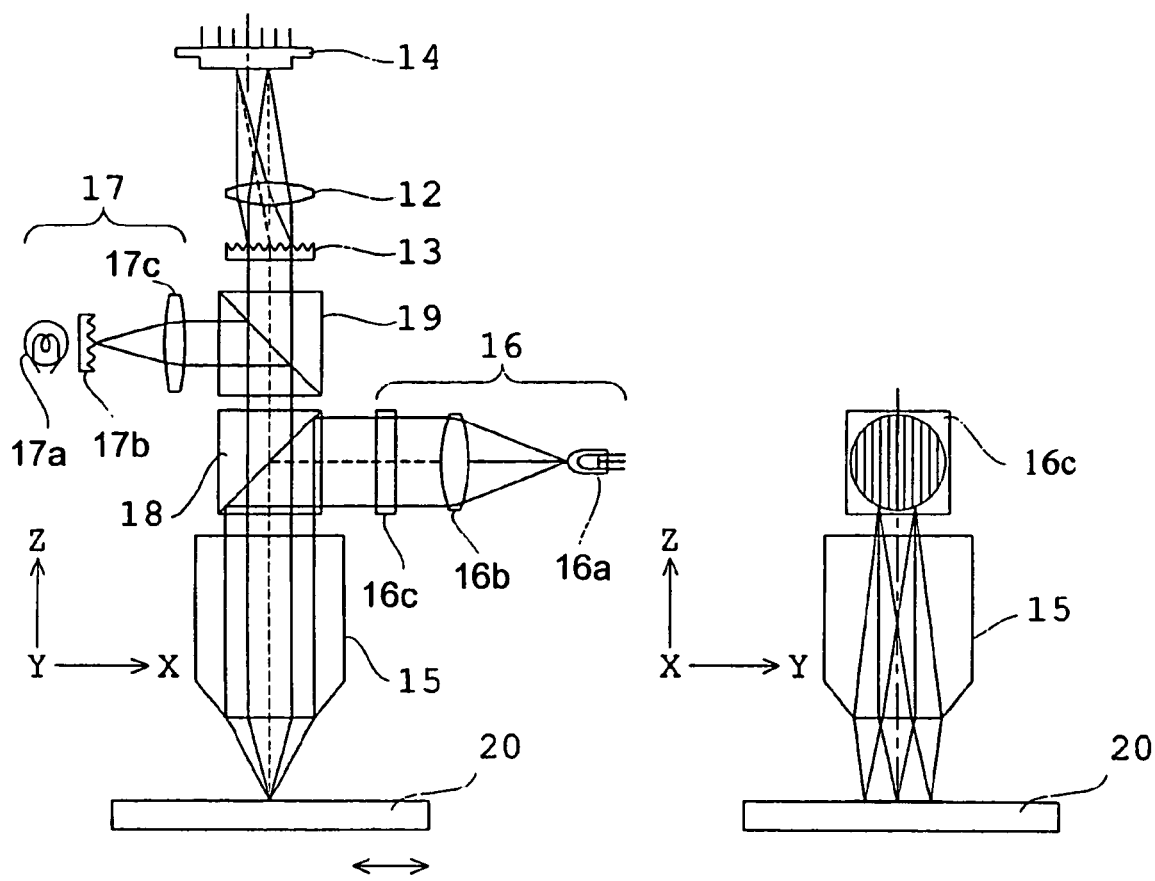
Fig. 14(a)
Fig. 14(c)
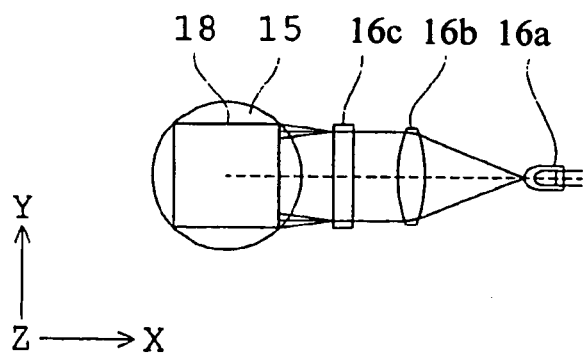
Fig. 14(b)

US 7,554,572 B2

IMAGE PICKUP APPARATUS FOR CAPTURING SPECTRAL IMAGES OF AN OBJECT AND OBSERVATION SYSTEM INCLUDING THE SAME

This application claims benefit under 35 U.S.C. §119 of JP 2004-154659, filed May 25, 2004, the contents of which are hereby incorporated by reference.

BACKGROUND OF THE INVENTION

The present invention relates to an image pickup apparatus for obtaining spectral images of an object, and particularly relates to an image pickup unit in a medical endoscope for obtaining spectral images of fluorescence emitted by living tissue, and an analysis device for analyzing obtained spectral images, such as measuring fluorescent wavelengths for living tissue diagnosis, and is also concerned with an image pickup unit in an industrial inspection device for obtaining spectral images of luminous surfaces such as those of LEDs and an analysis device for analyzing obtained spectral images, such as measuring spectroscopic properties of an object surface for quality control on a production line.

Devices in the prior art for measuring spectroscopic properties include those described in Japanese Laid Open Patent Application No. H02-104332 (which corresponds in subject matter to U.S. Pat. No. 5,078,150), in Japanese Laid Open Patent Application No. S63-271308, in U.S. Pat. No. 5,782,770, and in a document entitled "Spectral Camera" that was published on the Internet by DHT Corporation (found at: http://www.dht.co.jp/products/spectral camera/spectral camera.html).

Japanese Laid Open Patent Application No. H02-104332 discloses a spectroscopic endoscope in which illumination light is separated into multiple wave bands in a time-division manner via a rotating filter provided in the light source while continuously illuminating an object, thereby obtaining spectral images separated in a time-division manner.

Japanese Laid Open Patent Application No. S63-271308 discloses an endoscope having a variable transmittance element in the observation optical system wherein the wavelengths transmitted by the variable transmittance element may be successively changed, thereby enabling spectral images to be obtained for different wave bands.

U.S. Pat. No. 5,782,770 discloses a detection device in which a ribbon-shaped beam is used to illuminate an object, and spectral content of the image of the object is then detected via a dispersion element.

The Internet publication entitled "Spectral Camera" mentioned above discloses a spectral camera having a slit opening, a spectroscope, and a two-dimensional CCD camera in which light from an object is received via the slit opening and the light is then separated according to wavelength, thereby enabling the spectrum of an object to be obtained.

In the endoscopes for obtaining spectral images of an object described in Japanese Laid Open Patent Application Nos. H02-104332 and S63-271308 mentioned above, only object information carried by light of specific wavelength components from the object is imaged. For example, in a medical endoscope, only light of blue components reflected by the living tissue can be imaged to clearly depict the capillary blood vessels in the surface layer of the living tissue. In the endoscope described in Japanese Laid Open Patent Application No. S63-271308, a variable transmittance element is provided in the observation optical system. Thus, fluorescent images emitted by the object can be selectively obtained. However, it is difficult to obtain bands of smaller-wavelength separations using a rotating filter or a variable transmittance element. Therefore, high-resolution extraction of the spectrum of the object from obtained spectral images cannot be achieved.

On the other hand, with the devices for detecting the spectrum of an object described in U.S. Pat. No. 5,782,770, and in the document entitled "Spectral Camera" mentioned above, high resolution spectra can be obtained using a spectroscopic element. However, these devices do not provide color object images, making it impossible to examine the object while obtaining spectral information or to identify from which part of the object the spectral information is obtained. In order to obtain color images of an object using these devices, an image pickup optical system for obtaining color images must be additionally provided, or a mechanism for retracting the spectroscopic element from the optical path of the observation optical system must be provided, which alternatives are not desirable because this would require that the size of the device be increased.

BRIEF SUMMARY OF THE INVENTION

The present invention provides a small image pickup apparatus that simultaneously allows for high-resolution spectral images and color images of an object to be observed.

BRIEF DESCRIPTION OF THE DRAWINGS

The present invention will become more fully understood from the detailed description given below and the accompanying drawings, which are given by way of illustration only and thus are not limitative of the present invention, wherein:

FIGS. 4(a) and 4(b) are illustrations to explain the construction of the image pickup apparatus of Embodiment 2 of the present invention, with FIG. 4(a) being a cross-section containing the optical axis of the observation optical system that shows the basic construction of an image pickup apparatus 5, and with FIG. 4(b) being a view in the direction of the optical axis that shows the imaging areas of −1st-order light and zero-order light on the image pickup surface of a solid-state image pickup element 4;

FIGS. 6(a) and 6(b) are illustrations showing an exemplary construction of a first illumination device 112, with FIG. 6(a) being a cross-section containing the optical axis and showing a construction of the first illumination device 112, and with FIG. 6(b) being a perspective view showing an exemplary construction of a slit glass 112b;

FIGS. 7(a) and 7(b) are illustrations showing an exemplary construction of the optical system of the light source (item 55, shown in FIG. 5), with FIG. 7(a) being a cross-section containing the center lines of the light guides 113a and 113b of the optical system of the light source as seen, for example, in a top view, and FIG. 7(b) being a composite cross-sectional view that includes the center line of one light guide of the optical system of the light source as seen, for example, from one side;

FIGS. 9(a) and 9(b) are illustrations to explain the construction of the image pickup apparatus of Embodiment 4 of the present invention, with FIG. 9(a) being a cross-section containing the optical axis of the observation optical system that shows the basic construction of an image pickup apparatus 5, and FIG. 9(b) being a view in the direction of the optical axis that shows the imaging areas of plus first-order light (hereinafter +1st-order light) and zero-order light on the image pickup surfaces of the solid-state image pickup elements 4b and 4a, respectively;

FIGS. 10(a)-10(c) are illustrations to explain the construction of the observation system 201 of Embodiment 5 of the present invention, with FIG. 10(a) being a cross-section containing the optical axis of the observation optical system 2, with FIG. 10(b) being a view in the direction of the optical axis that shows the imaging areas of −1st-order light and zero-order light on the image pickup surface of a solid-state image pickup element 4 when a second illumination device 7 extensively illuminates the object surface, and with FIG. 10(c) being a view in the direction of the optical axis that shows the imaging areas of −1st-order light and the zero-order light on the image pickup surface of a solid-state image pickup element 4 when a first illumination device 6 illuminates a narrow region of the object surface;

FIGS. 14(a)-14(c) are illustrations to explain the construction of an observation system for measuring spectral reflectance according to Embodiment 6 of the present invention, with FIG. 14(a) being a cross-section containing the optical axis of the objective lens 15 showing the basic construction of an observation system for measuring spectral reflectance, with FIG. 14(b) showing an illumination light flux of an illumination device 16 as viewed in the direction z, and with FIG. 14(c) showing an illumination light flux of the illumination device 16 as viewed in the direction x;

DETAILED DESCRIPTION

The image pickup apparatus of the present invention includes a diffraction element in the optical path of an observation optical system whereby zero-order light transmitted through the diffraction element and ±1st-order light diffracted by the diffraction element are imaged on the image pickup surface of an image pickup element, and the imaging areas of the zero-order light and ±1st-order light are not overlapped on the image pickup surface of the image pickup element. Therefore, a color image of an object can be observed within the area that receives the zero-order light and the spectrum of the object can be observed within the respective areas that receive the +1st-order light and the −1st-order light while preventing flare from occurring in these light-receiving areas.

As described above, a diffraction element is provided in the optical path of an observation optical system and both color image observation and spectrum detection of an object can be achieved. Therefore, for example, a small image pickup apparatus can be realized that can be provided at the insertion end of an endoscope. Further, morphological information of an object obtained from a color image, and spectral information of each part of the object can be analyzed and associated with each other.

Several embodiments of the present invention will now be described with reference to the drawings.

Embodiment 1

Figures 1A, 1B:
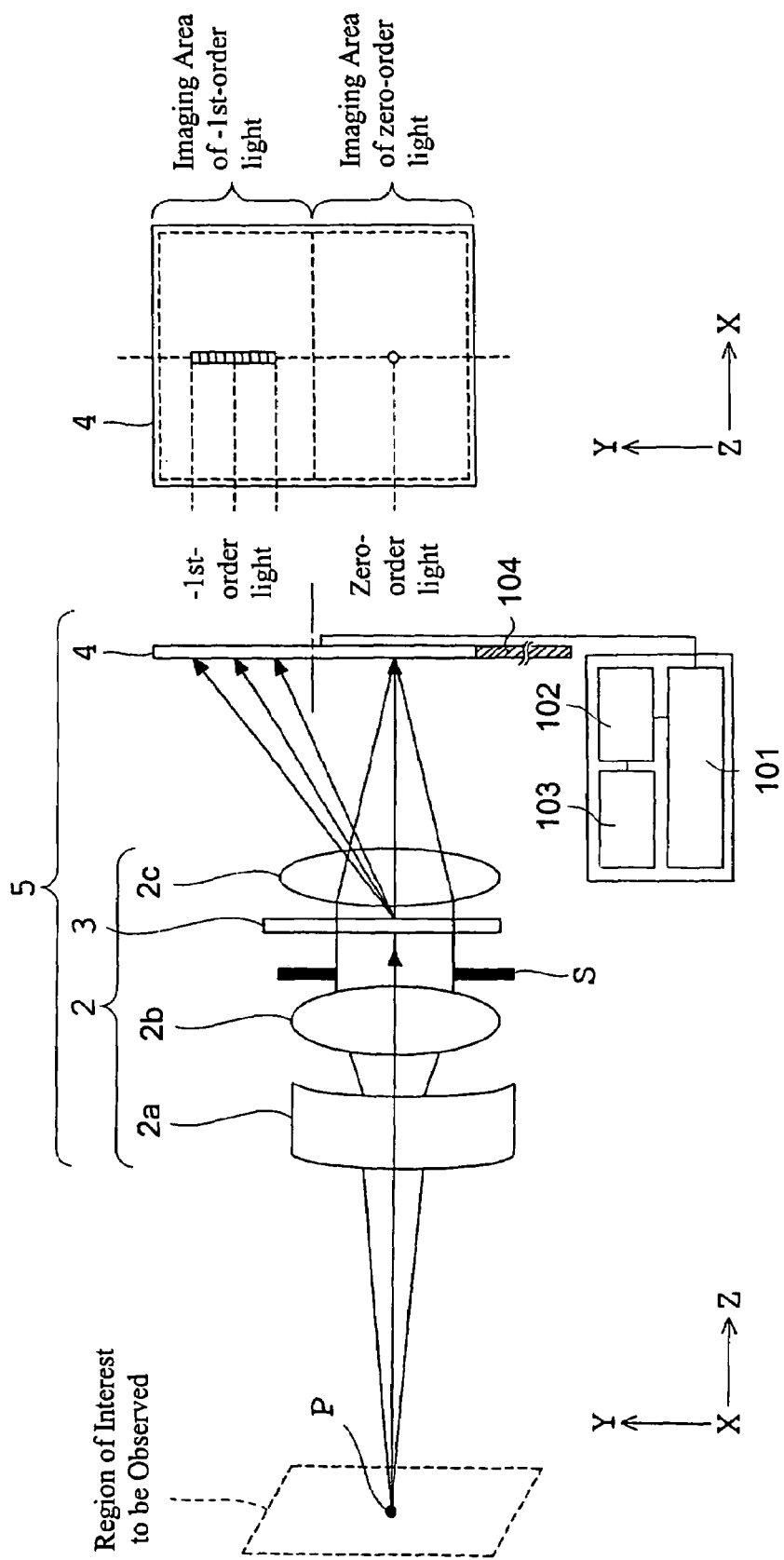
FIGS. 1(a) and 1(b) show the construction of the image pickup apparatus of Embodiment 1, with FIG. 1(a) being a cross-section containing the optical axis of the observation optical system that shows the basic construction of an image pickup apparatus 5, and with FIG. 1(b) being a view along the optical axis that shows the imaging areas of minus first order light (hereinafter referred to as −1st-order light) and zero-order light on the image pickup surface of a solid-state image pickup element.

The construction of an image pickup apparatus according to Embodiment 1 of the present invention will now be described with reference to FIGS. 1(a) and 1(b). FIG. 1(a) is a cross-section containing the optical axis of the observation optical system that shows the basic construction of an image pickup apparatus 5, and FIG. 1(b) is a view along the optical axis that shows the imaging areas of −1st-order light and zero-order light on the image pickup surface of a solid-state image pickup element. The image pickup apparatus 5 of the present invention is formed of an observation optical system 2 that includes a diffraction element 3 located in the optical path, and a solid-state image pickup element 4. The observation optical system 2 includes a lens 2a provided on the object surface side, and a collimating lens 2b for collimating a light flux from the lens 2a. In addition, the observation optical system 2 includes a diaphragm S and the diffraction element 3, each of which is located in the collimated light flux from the collimating lens 2b, and a lens 2c for imaging zero-order light that passes straight through the diffraction element 3 and −1st-order light that is diffracted by the diffraction element 3 onto off-axis positions on the image pickup surface of the solid-state image pickup element 4.

The diffraction element 3 is a transmission-type DOE (Diffractive Optical Element) such as a diffraction grating, or an HOE (Holographic Optical Element) such as a holographic film. Upon entering the diffraction element 3, light flux is separated into zero-order light and −1st-order light and +1st-order light. The ±1st-order light emerges from the diffraction element 3 at equal (plus and minus) angles to the optical axis, with the specific angle amount depending upon the wavelength of the incident light.

The solid-state image pickup element 4 is provided in a manner such that the center of the image pickup surface is not aligned with the optical axis of the observation optical system 2. The zero-order light that passes straight through the diffraction element 3 and the −1st-order light that is diffracted by the diffraction element 3 are imaged on the image pickup surface by the lens 2c. As shown in FIG. 1(b), the imaging areas of the zero-order light and −1st-order light do not overlap on the image pickup surface.

The spectrum of the −1st-order light from an object can be obtained by using the positional relationship between the imaging position of the −1st-order light and that of the zero-order light on the image pickup surface of the solid-state image pickup element 4. Here, it is assumed that a light beam emitted from a point on the object surface of an object is imaged on the image pickup surface of the solid-state image pickup element 4 via the observation optical system. The relationship between the imaging position of the zero-order light and the spectrum of the −1st-order light on the image pickup surface of the solid-state image pickup element 4 will now be explained with reference to FIGS. 2(a) through 3(c).

Figure 2A:
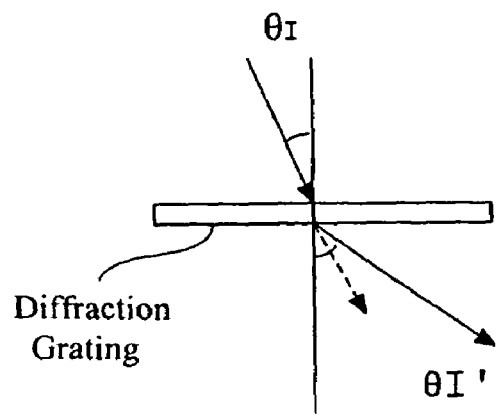
FIGS. 2(a) and 2(b) are illustrations to explain the relationship between the imaging position of zero-order light and the spectral position of −1st-order light of a diffraction grating used in the spectroscopic element of the present invention, with FIG. 2(a) showing the diffraction of the principal ray of an imaging light flux when the diffraction element is a transmission-type diffraction grating, and with FIG. 2(b) showing the different imaging positions of different wavelengths due to dispersion of the diffraction grating.

FIG. 2(a) is an illustration showing the diffraction of the principal ray of a light flux when the diffraction element 3 is a transmission-type diffraction grating. Assuming the incident angle of a wavelength $\lambda$ relative to the optical axis of the diffraction grating is $\theta I$ and the diffraction angle is $\theta I'$ as shown in FIG. 2(a), the following Equation (1) is obtained:

$$\sin\theta I - \sin\theta I' = N \cdot \lambda / d \qquad \text{Equation (1)}$$

where

N is the order of diffraction (here, N=−1), and d is the diffraction grating pitch.

Figure 2B:
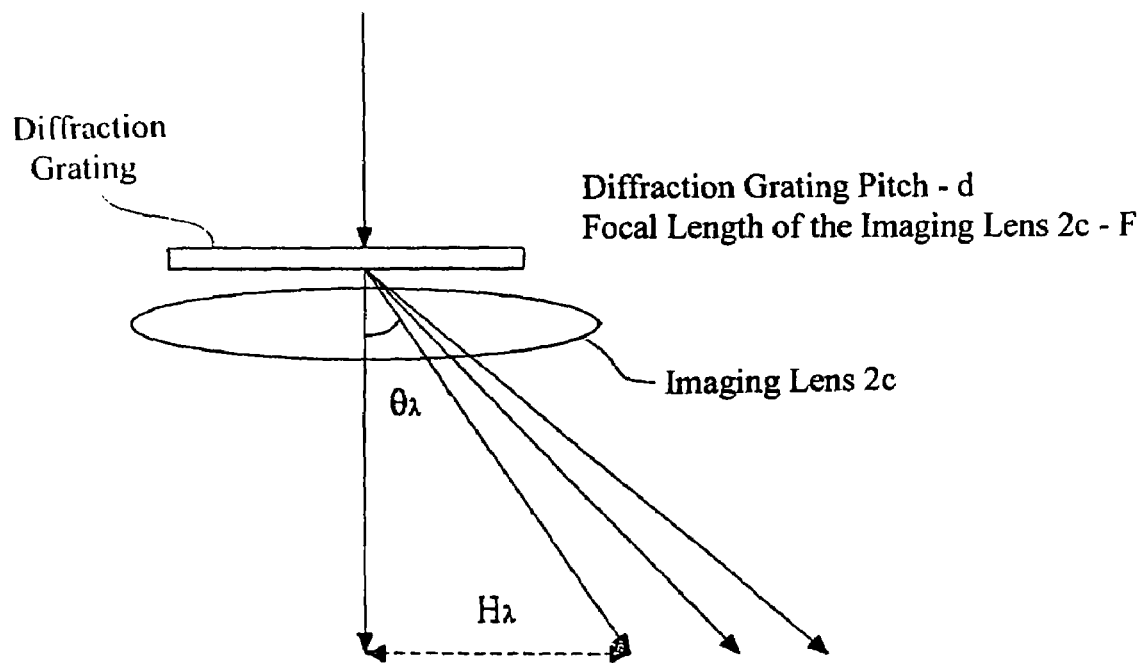

It is assumed that the diffraction element 3 is provided in the collimated light flux and the imaging lens 2c is provided behind the diffraction element 3, as in this embodiment. FIG. 2(b) schematically shows the different imaging positions for different wavelengths as a result of the dispersion of the diffraction grating. Provided that the imaging lens 2c is a lens having distortion of a sin θ type, the following Equations (2) and (3) are obtained for a diffraction angle $\theta\lambda$ for each wavelength of the principal ray entering the diffraction grating at a right angle:

$$-\sin\theta\lambda = N \cdot \lambda / d \qquad \text{Equation (2)}$$

$$H_\lambda = -F \cdot \sin\theta\lambda = F \cdot N \cdot \lambda / d \qquad \text{Equation (3)}$$

where $H_\lambda$ is the image height on the imaging surface of the diffracted light having a wavelength $\lambda$, F is the focal length of the imaging lens 2c, and N and d are as previously defined.

As the incident angle $\theta I$ of the principal ray of an imaging light flux entering the diffraction grating is changed, the imaging positions of the zero-order light and the −1st-order light are accordingly shifted. Here, it is assumed for convenience that the diffraction grating causes dispersion, but does not cause refraction or imaging. Such a diffraction grating allows the zero-order light to pass straight through the diffraction grating so that the exit angle is the same as the incident angle.

Figure 3A:
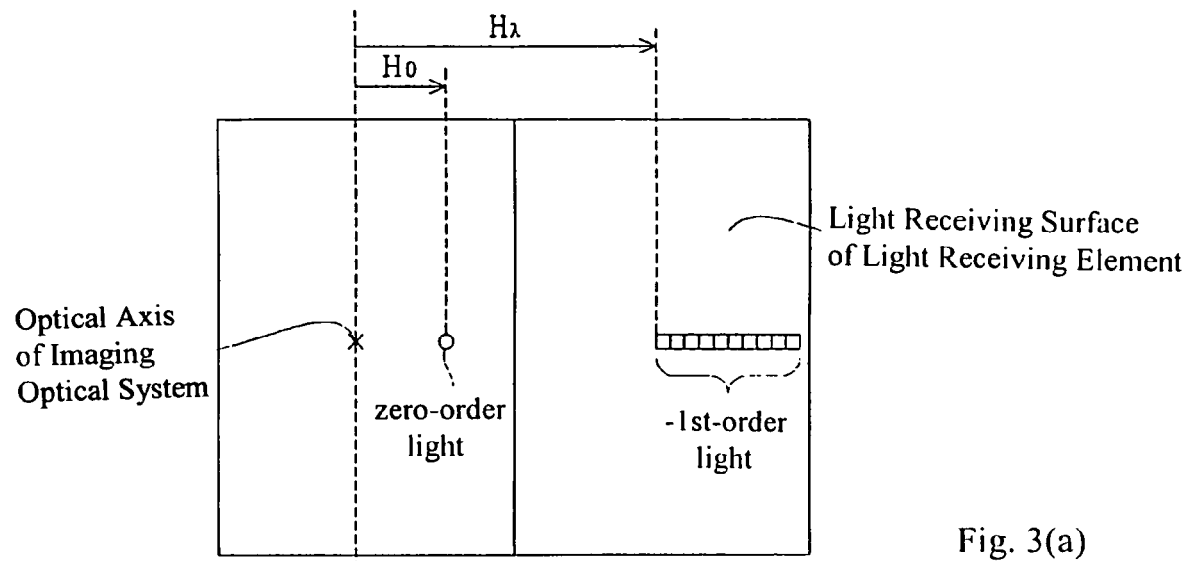
FIGS. 3(a)-3(c) are illustrations to schematically show the relationship between the imaging positions of the zero-order light and the −1st-order light on the image pickup surface of a solid-state image pickup element; with the incident light having an angle of incidence of +θI degrees in FIG. 3(a), 0 degrees in FIG. 3(b), and −θI degrees in FIG. 3(c).
Figure 3B:
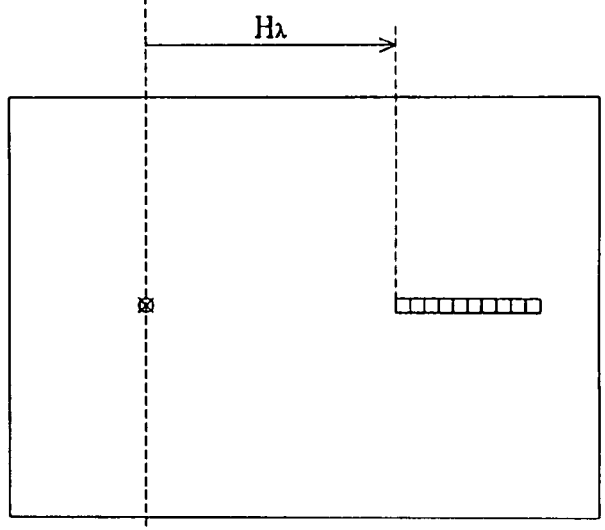
Figure 3C:
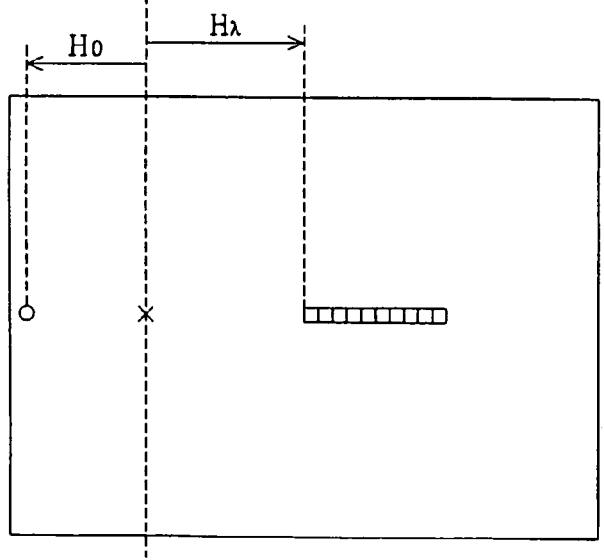

FIGS. 3(a)-3(c) show the positional relationship between the imaging positions of the zero-order light and the −1st-order diffracted light on the image pickup surface of the solid-state image pickup element 4 for three different incidence angles of incident light onto the diffraction grating. In FIGS. 3(a)-3(c), the position on the image pickup surface that corresponds to the optical axis of the imaging optical system is marked with an "x" in each figure. In FIG. 3(a), the image position on the image pickup surface labeled "zero-order light" is the image position of light from an object point located off the optical axis such that a principal ray enters the diffraction grating at the angle $+\theta I$ (see FIG. 2(a)), and this position is at a distance $H_0$ to the right of the optical axis "x" position of the imaging optical system. In this case, the position of the −1st-order diffracted light is at a distance $H_\lambda$ from the optical axis that is relatively far from the optical axis. FIG. 3(b) illustrates the situation where the angle of incidence of the incident light is such that the zero-order diffracted light travels along the optical axis and thus the image of the zero-order light lies at the position "x". Zero-order light from the point on the object at zero image height, i.e., the point on the object that corresponds to the optical axis of the imaging optical system, passes straight through the diffraction grating and thus is imaged at the point "x" on the image pickup surface. In this case, the position of the −1st-order diffracted light is at a distance $H_\lambda$ from the optical axis that is a medium distance from the optical axis. FIG. 3(c) illustrates the situation where the angle of incidence of the incident light is such that a principal ray enters the diffraction grating at the angle $-\theta I$, and this light is imaged onto the image pickup surface at a position to the left of the optical axis at a distance $H_0$. In this case, the position of the −1st-order diffracted light is at a distance $H_\lambda$ from the optical axis that is relatively near the optical axis.

The relationship between the imaging position of the zero-order light and the position of the spectrum of the −1st-order light is given by the following Equation (4):

$$\sin\theta I - \sin\theta I'_\lambda = N \cdot \lambda / d \qquad \text{Equation (4)}$$

where $\theta I$ is the incident angle of light having a wavelength $\lambda$ relative to the optical axis of the diffraction element, $\theta I'_\lambda$ is the diffraction angle of light having a wavelength $\lambda$ relative to the optical axis of the diffraction element, and N and d are as previously defined.

When the imaging lens 2c behind the diffraction grating is a lens having distortion of sin θ type, the image height $H_\lambda$ on the image pickup surface of the −1st-order light having a wavelength $\lambda$ is obtained using the following Equation (5):

$$H_\lambda = -F \cdot \sin\theta I'_\lambda \qquad \text{Equation (5)}$$

where $H_\lambda$, F, and $\theta I'_\lambda$ are as previously defined.

On the other hand, the image height $H_0$ on the image pickup surface of the zero-order light is obtained using the following Equation (6):

$$H_0 = -F \cdot \sin\theta I \qquad \text{Equation (6)}$$

where

F and $\theta I$ are as previously defined.

The distance between the imaging positions of the zero-order light and the −1st-order light having a wavelength λ is given by the following Equation (7):

$$H_\lambda - H_0 = -F \cdot \sin\theta I'_\lambda - (-F \cdot \sin\theta I) \quad \text{Equation (7)}$$
$$= F(\sin\theta I - \sin\theta I'_\lambda)$$
$$= F \cdot N \cdot \lambda / d$$

It is understood from Equation (7) that the distance between the imaging positions of the zero-order light and the −1st-order light having a wavelength λ is constant regardless of the incident angle of the principal ray to the diffraction grating. Therefore, detecting the imaging position of the zero-order light leads to identifying the imaging position of the spectrum of the −1st-order light. In this embodiment, the imaging lens 2c behind the diffraction grating is a lens having distortion that varies according to sin θ. Practically speaking, a similar calculation may be applied to a lens having any type of distortion provided that its aberration properties are previously measured and known.

The imaging position of the spectrum of the −1st-order light is identified as follows.

(1) The image height $H_0$ of the zero-order light (i.e., the imaging position of the zero-order light) is measured based on an image acquired by the solid-state image pickup element 4;

(2) The incident angle θI onto the diffraction grating of the principal ray is calculated using the image height $H_0$ of the zero-order light, the previously measured focal length F, and distortion property of the imaging lens 2c;

(3) The diffraction angle $\theta I'_\lambda$ of the −1st-order light having a wavelength λ is calculated using the incident angle θI (as determined in step (2) above), the diffraction grating pitch d, the order of diffraction N, and the wavelength λ; and (4) The image height $H_\lambda$ of the −1st-order light having a wavelength λ is calculated for a diffraction angle $\theta I'_\lambda$ for light of wavelength λ as calculated in step (3), the previously measured focal length F and the distortion properties of the imaging lens 2c.

Based on the imaging position of the spectrum of the −1st-order light as described above and the intensity of image pickup signals at each position, analysis of the intensity property of the spectrum of the obtained image may be performed.

In practice, a coordinate is assumed on the image pickup surface of the solid-state image pickup element 4 having an origin at the intersection with the optical axis of the observation optical system. Referring again to FIG. 1(a), the image pickup apparatus 5 is provided with an image analysis circuit 101 for analyzing the position of an obtained image and an arithmetic operation circuit 102 for executing the calculations above to acquire the spectral properties of the obtained image on a real time basis.

When holographic techniques are applied to the diffraction element, a diffraction grating that performs imaging in addition to providing a diffraction function can be provided. With the use of such a diffraction grating, the imaging lens 2c behind the diffraction grating can be eliminated. The focal length F and the distortion property of the diffraction grating may be measured and stored in a memory 103 as a calculation parameter. An arithmetic operation circuit may perform the calculations above by using the stored parameter, thereby enabling the arithmetic operations to be repeatedly executed.

The image pickup apparatus 5 of the present invention is provided with an illumination device. It is desired that the illumination device have a function to extensively illuminate an object and also functions to spotlight a small part of the object.

When the illumination device extensively illuminates an object, the entire image of the object is obtained in the imaging area of the zero-order light on the image pickup surface of the solid-state image pickup element 4. Concurrently, spectral images of the entire object are obtained in the imaging area of the −1st-order light on the image pickup surface. When illumination refers to emitted white light, a color object image and respective object images for different wavelengths are obtained in a successively overlapped manner. In the latter images, the spectral information for each point of the object is superimposed. Therefore, it is difficult to analyze the spectral information based on the calculations described above.

Hence, the illumination device in this embodiment has the function of spotlighting a small portion of the object, thereby enabling the spectral information for each point of the object to be separately obtained in the imaging area of the −1st-order light on the image pickup surface of the image pickup element 4.

For example, an object may be extensively illuminated in one instance and only a small part of the object may be illuminated (i.e., spotlighted) in another instance. Then, a color image obtained by extensively illuminating the object and a spectral image obtained by spotlighting a small part of the object may be merged and displayed by a display. In this manner, the spectrum at a specific point of the object can be observed while examining the appearance of the object. The spot image obtained in the imaging area of the zero-order light on the image pickup surface of the solid-state image pickup element 4 during the spotlighting can be analyzed according to its coordinates. Then, the color object image obtained by extensively illuminating the object can be marked in the position where the spot image is taken, thereby enabling the positions on the object where the spectral information of the object comes from to be known.

In this embodiment, the image pickup surface of the solid-state image pickup element 4 receives the zero-order light that is transmitted straight through the diffraction element 3 and the −1st-order light that is diffracted by the diffraction element 3. The +1st-order light diffracted by the diffraction element 3 and higher-order diffractive components are unnecessary for image pickup. Therefore, it is desirable to eliminate those light beams by providing optical members, in combination, that reflect or absorb the light beams between the diffraction element 3 and the image pickup surface. For example, a light absorbing member 104 can be provided at the imaging area of +1st-order light along with the solid-state image pickup element 4, thereby eliminating the +1st-order light from being detected by the solid-state image pickup element 4.

Embodiment 2

The construction of an image pickup apparatus according to Embodiment 2 of the present invention will now be described with reference to FIGS. 4(a) and 4(b). FIG. 4(a) is a cross-section containing the optical axis of the observation optical system showing the basic construction of the image pickup apparatus 5. FIG. 4(b) is an illustration showing the imaging areas of the −1st-order light and zero-order light on the image pickup surface of a solid-state image pickup element 4, as viewed from a position on the optical axis facing the image pickup surface.

The image pickup apparatus 5 of Embodiment 2 of the present invention is formed of an observation optical system 2 which may include a diffraction element 3 located in the optical path, and a solid-state image pickup element 4. The observation optical system 2 is formed of a lens 2a located on the object surface side of the observation optical system 2, a collimating lens 2b for collimating a light beam from the lens 2a, and a diaphragm S and the diffraction element 3 located within the collimated light flux.

The diffraction element 3 is a transmission-type diffraction grating that provides an imaging function in addition to providing a diffraction function. Entering the diffraction element 3, a light flux is separated into zero-order light and ±1st-order light due to diffraction. The ±1st-order light emerges from the diffraction element 3 at equal but opposite angles to the optical axis, with the angle amount depending on the wavelength of the light, and is then incident onto the image pickup surface of the image pickup element 4.

The solid-state image pickup element 4 is positioned in a manner such that the center of the image pickup surface is not aligned with the optical axis of the observation optical system 2. It thereby receives the light fluxes of the zero-order light and −1st-order light from the diffraction element 3. As shown in FIG. 4(b), the imaging areas of the zero-order light and −1st-order light do not overlap on the image pickup surface.

Figure 5:
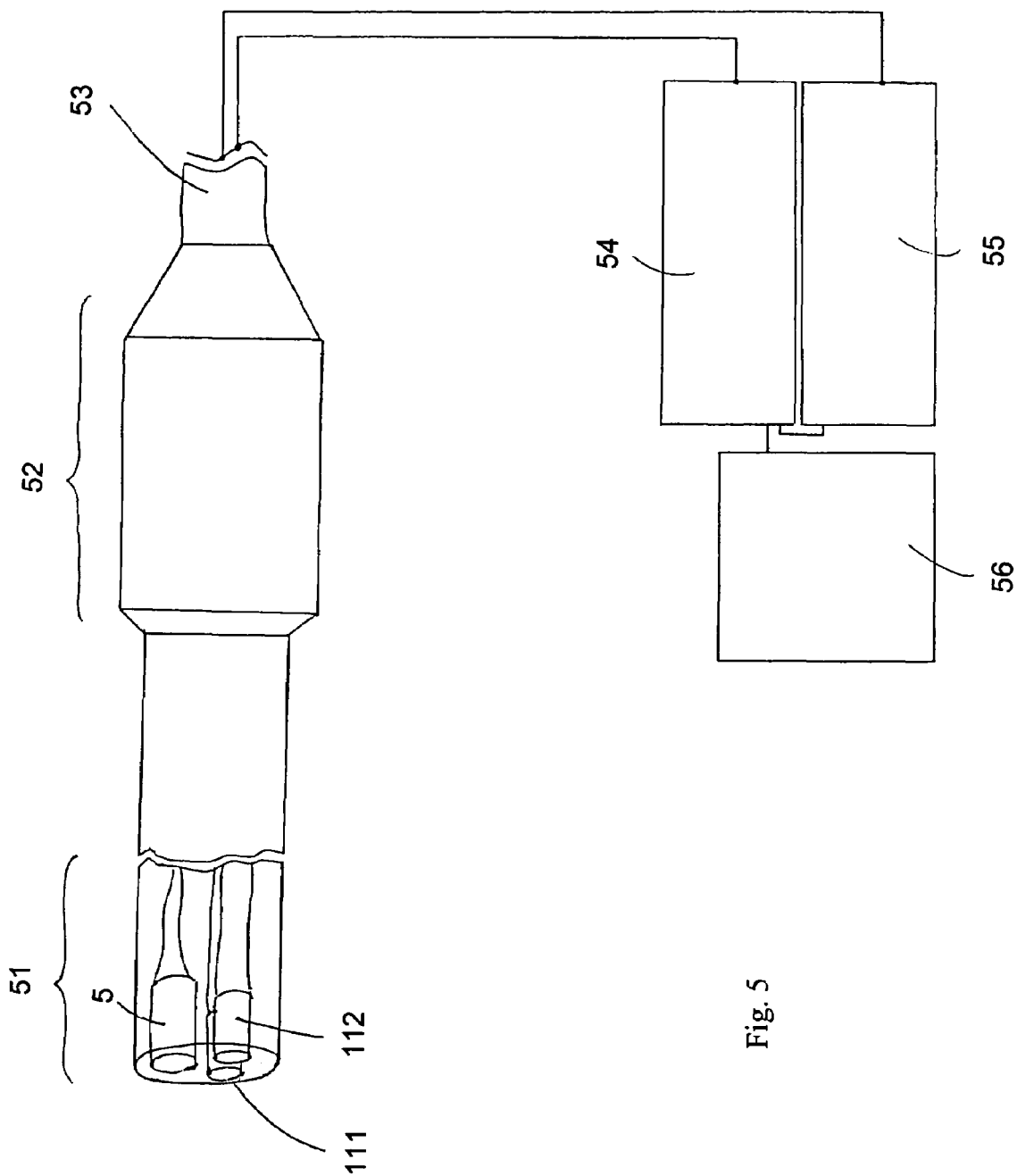
FIG. 5 is an illustration showing the construction of an endoscope system in which the image pickup apparatus 5 is mounted.

With this construction, the image pickup apparatus 5 can be downsized so that it can be mounted at, for example, the insertion end of an endoscope. FIG. 5 shows an example of an endoscope in which the image pickup apparatus 5 is mounted at the insertion end of the endoscope. The image pickup apparatus 5 is provided at the leading end 51 with a first illumination device 112 for illuminating a relatively narrow area of an object via a slit opening, and a second illumination device 111 for extensively illuminating an object. Image signals obtained by the image pickup apparatus 5 are transferred to an image processing device 54 via a universal cable 53 extended from an operation part 52 of the endoscope. The image processing device 54 includes an image analysis circuit 101 (not shown in FIG. 5), an arithmetic operation circuit 102 (not shown in FIG. 5), and a memory as described above to analyze and merge obtained images. Images that are processed by the image processing device 54 may be displayed by a display device 56.

FIGS. 6(a) and 6(b) show an exemplary construction of the first illumination device 112. FIG. 6(a) is a cross-section showing the construction of the first illumination device 112. Illumination light supplied by a light source 55 is transferred to the first illumination device 112 via a light guide 113a provided in the universal cable 53. Light emerging from the exit end of the light guide 113a enters a single fiber rod lens 112a. The single fiber rod lens 112a allows the light to emerge from the exit end thereof with a nearly uniform intensity. Light passing through the linear opening in a slit glass 112b illuminates an object surface via a projection lens 112c. FIG. 6(b) shows an exemplary construction of the slit glass 112b. The slit glass 112b has a linear slit printed on one surface of a parallel flat glass and an anti-reflection coating deposited on the other surface. A super-thin metal plate with a linear slit can be used in place of the slit glass 112b. The second illumination device 111 can have any construction that allows extensive illumination of an object. For example, a planoconvex lens with the flat surface on the object side can be provided immediately after the exit end of a light guide 113b (FIG. 7(a)), thereby allowing light emerging from the light guide 113b to illuminate the object in a diffuse manner.

FIGS. 7(a) and 7(b) show an exemplary construction of the light source 55. FIG. 7(a) is a cross-section containing the center lines of the light guides 113a and 113b of the optical system of the light source 55 shown in FIG. 5 as seen, for example, in a top view, and FIG. 7(b) is a composite cross-sectional view that includes the center line of one light guide of the optical system of the light source 55 as seen, for example, from one side. Light that emerges from a discharge lamp 117 is collected on the entrance end of the light guide 113a, 113b by a relay optical system 116 and collection lenses 114a, 114b. Collection lens 114a supplies light to the first illumination device 112 and collection lens 114b supplies light to the second illumination device 111. An optical path-switching mirror 115 is provided in the optical path of the relay optical system 116. The mirror is rotated about a line including the intersection with the relay optical system 116 in order to switch between the optical paths of the collection lenses 114a and 114b. When the optical path of the collection lens 114a is selected, light from the light source 117 is directed to the light guide 113a so that the first illumination device 112 illuminates a relatively narrow area of an object. When the optical path of the collection lens 114b is selected, light from the light source 117 is directed to the light guide 113b so that the second illumination device 111 extensively illuminates an object. A glass rod is provided at the entrance end of each of the light guides 113a, 1113b, thereby preventing the entrance ends of the light guides 113a, 113b from being damaged by the thermal energy of the collected light.

The image processing device 54 is electrically connected to the light source 55 and controls the switching between extensive illumination of an object and linear illumination of a small part of the object. The optical path switching mirror 115 provided in the optical system of the light source 55 is controlled based on control signals transmitted from a control circuit built in the image processing device 54.

When the second illumination device 111 extensively illuminates an object, the entire image of the object is obtained in the imaging area of the zero-order light on the image pickup surface of the solid-state image pickup element 4. Concurrently, spectral images of the entire object are obtained in the imaging area of the −1st-order light on the image pickup surface. When the illumination device emits white light, a color object image and respective object images for different wavelengths are obtained in a successively overlapping manner. It is difficult to analyze the spectral information using the latter images because the spectral information at each point of the object is overlapped. Therefore, in this embodiment, the first illumination device 112 serves to illuminate a relatively narrow area of the object. Thus, the object surface is divided into segments in the imaging area of the −1st-order light on the image pickup surface of the solid-state image pickup element 4, yielding separate spectral information.

Embodiment 3

Figures 8A, 8B:
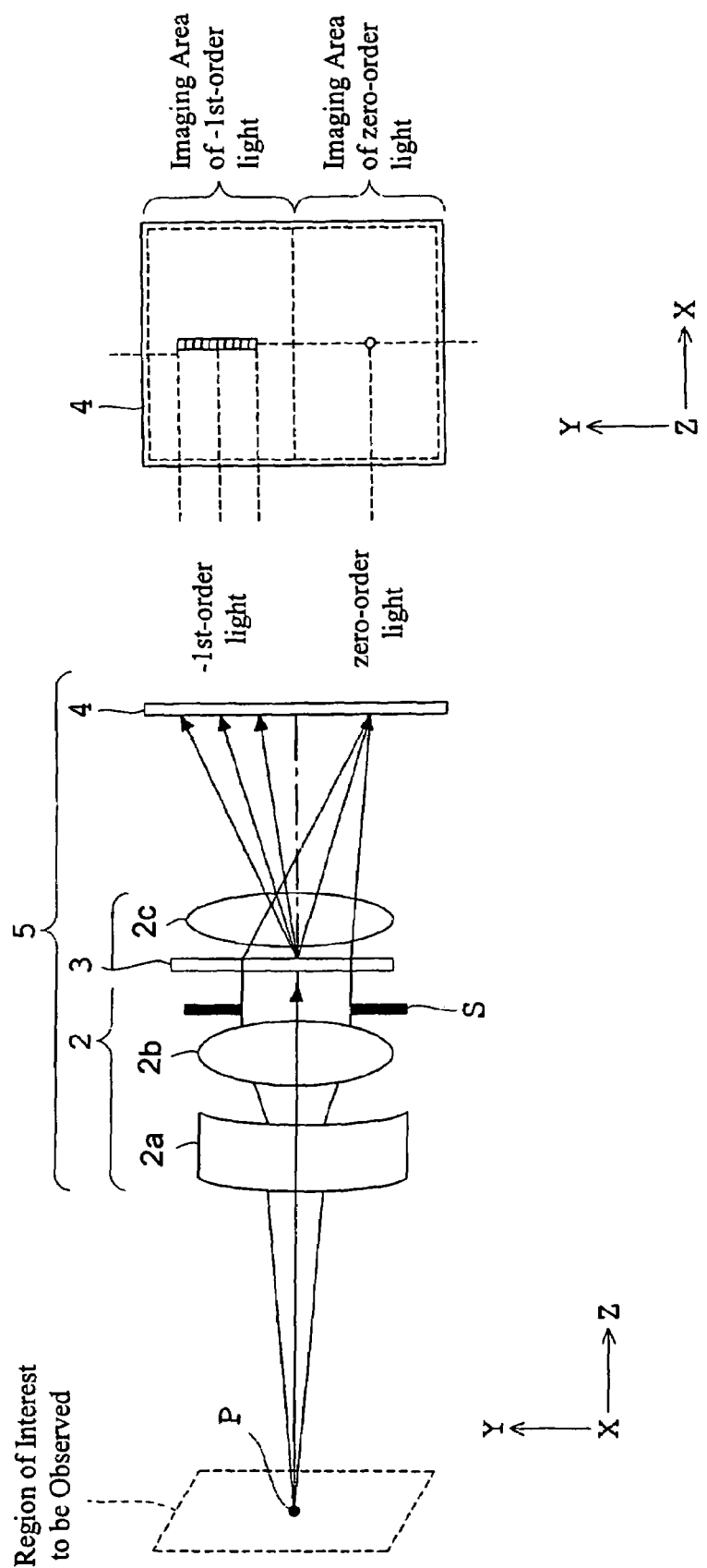
FIGS. 8(a) and 8(b) are illustrations to explain the construction of the image pickup apparatus of Embodiment 3 of the present invention, with FIG. 8(a) being a cross-section containing the optical axis of the observation optical system that shows the basic construction of an image pickup apparatus 5, and FIG. 8(b) being a view in the direction of the optical axis that shows the imaging areas of −1st-order light and zero-order light on the image pickup surface of a solid-state image pickup element 4.

The construction of an image pickup apparatus according to Embodiment 3 of the present invention will now be described with reference to FIGS. 8(a) and 8(b). FIG. 8(a) is a cross-section containing the optical axis of the observation optical system that shows the basic construction of an image pickup apparatus 5, and FIG. 8(b) is a view in the direction of the optical axis that shows the imaging areas of −1st-order light and zero-order light on the image pickup surface of a solid-state image pickup element 4.

The image pickup apparatus 5 of this embodiment is formed of an observation optical system 2 which includes a diffraction element 3 located in the optical path, and a solid-state image pickup element 4. The observation optical system 2 is formed of a lens 2a on the object surface side of the observation optical system, a collimating lens 2b for collimating a light flux from the lens 2a, a diaphragm S and a diffraction element 3 provided in the collimated light flux, and an imaging lens 2c for imaging the zero-order light that is transmitted straight through the diffraction element 3 and the −1st-order light that is diffracted by the diffraction element 3. The zero-order light and the −1st-order light are received onto the image pickup surface of the solid-state image pickup element 4. The diffraction element 3 is a transmission-type diffraction grating that provides a refraction function in addition to performing a diffraction function. A light flux that enters the diffraction element 3 is separated into zero-order light, +1st-order light, and −1st-order light due to diffraction. The zero-order light, the +1st-order light, and the −1st-order light emerge at different angles due to refraction. The refraction directions can be controlled to adjust the imaging positions of the zero-order light, the +1st-order light, and the −1st-order light. For example, the solid-state image pickup element 4 may be positioned in a manner such that the center of the image pickup surface coincides with the optical axis of the observation optical system 2 and such that the image pickup surface receives the imaging light fluxes of the zero-order light and the −1st-order light that emerge from the diffraction element 3.

As shown in FIG. 8(b), the imaging areas of the zero-order light and −1st-order light do not overlap on the image pickup surface. In this case, the refraction angle and direction of the diffraction element 3 can be pre-measured and stored as parameters to be used in calculations (in addition to the focal length F and distortion property of the imaging lens 2c) in order to identify the imaging positions of the zero-order light and the spectrum of the −1st-order light.

The image pickup apparatus 5 having the construction above in which the center of the image pickup surface coincides with the optical axis of the observation optical system 2 is preferably provided at the insertion end of an endoscope because it allows the insertion end of the endoscope to have a smaller outer diameter. This embodiment is nearly the same as that of Embodiment 1 in terms of its construction and its efficacy.

Embodiment 4

The construction of an image pickup apparatus according to Embodiment 4 of the present invention will now be described with reference to FIGS. 9(a) and 9(b). FIG. 9(a) is a cross-section containing the optical axis of the observation optical system that shows the basic construction of an image pickup apparatus 5, and FIG. 9(b) is a view in the direction of the optical axis that shows the imaging areas of plus first-order light (hereinafter +1st-order light) and zero-order light on the image pickup surfaces of the solid-state image pickup elements 4b and 4a, respectively.

The image pickup apparatus 5 of this embodiment is formed of an observation optical system 2, which includes a diffraction element 3 located in the optical path of the observation optical system 2, and two solid-state image pickup elements 4a and 4b. The observation optical system 2 is formed of a lens 2a on the object surface side of the observation optical system 2, a lens 2b for imaging a light flux from the lens 2a on the image pickup surfaces of the solid-state image pickup elements 4a and 4b, and a diffraction element 3 that is provided at a specific angle in the imaging light flux. The diffraction element 3 is a reflection-type diffraction grating that has a reflecting function in addition to having a diffraction function. Upon being incident onto the diffraction element 3, a light flux is separated into zero-order light, +1st-order light, and −1st-order light upon being diffracted. The zero-order light, the +1st-order light, and the −1st-order light emerge at different angles due to diffraction. The solid-state image pickup elements 4a and 4b are provided at the image plane of the zero-order light and the +1st-order light, respectively, in such a manner that the centers of their image pickup surfaces each coincide with the optical axis of the observation optical system.

As before, coordinates having an origin on the image pickup surfaces of the solid-state image pickup elements 4a and 4b at the intersections with the optical axis of the observation optical system are assumed in the image pickup apparatus 5. An image analysis circuit 101 (not shown in FIG. 9(a)) for analyzing the position of an obtained image and an arithmetic operation circuit 102 (not shown in FIG. 9(a)) for executing calculations required to analyze spectral information and to create an image may be provided. In this manner, the spectral properties of the obtained image may be acquired on a real time basis. The focal length F and distortion properties of the lenses 2a and 2b may be previously measured and stored in a memory 103 (not shown in FIG. 9(a)). An arithmetic operation circuit may use these as parameters in calculations in order to identify the imaging positions of the zero-order light and the spectrum of the +1st-order light on the image pickup surface. These circuits have the same construction as those in Embodiment 1 and, therefore, are not further illustrated.

The image pickup apparatus of this embodiment, wherein solid-state image pickup elements 4a and 4b are provided at the image plane of the zero-order light and the +1st-order light, respectively, allows for larger imaging areas on the image pickup surface as compared with the case where a single solid-state image pickup element is used to pick up images. Therefore, spectral information can be analyzed with higher resolution for the same object image range.

Embodiment 5

Figure 10A:
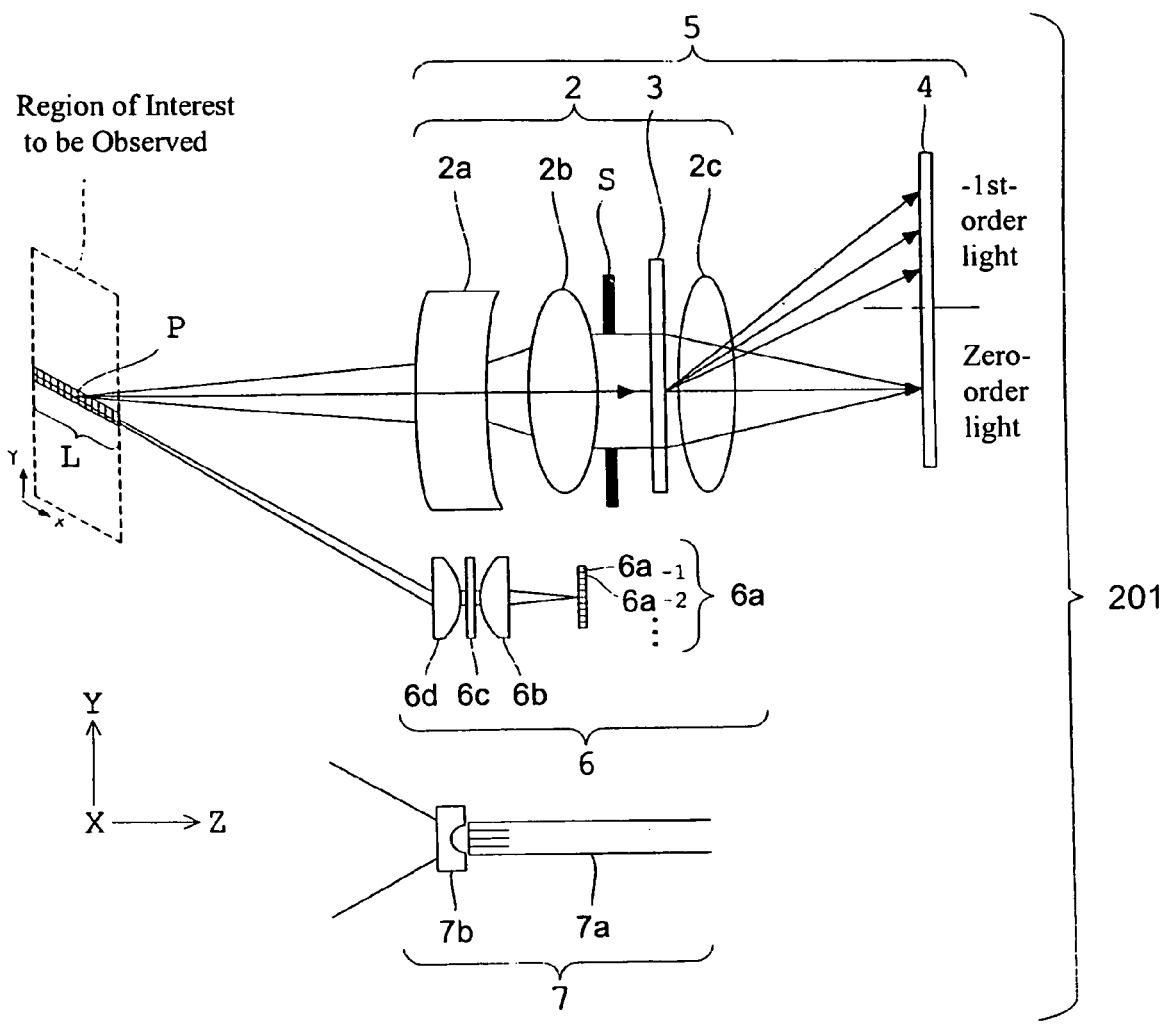

The construction of an observation system 201 according to Embodiment 5 of the present invention will now be described with reference to FIGS. 10(a)-10(c). FIG. 10(a) is a cross-section containing the optical axis of the observation optical system 2 showing the basic construction of the observation device 201 of this embodiment. FIG. 10(b) is an illustration showing the imaging areas of −1st-order light and zero-order light on the image pickup surface of a solid-state image pickup element 4 when the object surface is illuminated by the second illumination device 7. FIG. 10(c) is an illustration showing the imaging areas of −1st-order light and zero-order light on the image pickup surface of a solid-state image pickup element 4 when the object surface is illuminated by the first illumination device 6. In FIG. 10(a), the object surface is shown in a perspective view for greater clarity of explanation.

The observation system 201 of this embodiment is formed of an image pickup apparatus 5 that has the same construction as in Embodiment 1, a first illumination device 6 for illuminating a narrow linear region part of an object surface, and a second illumination device 7 for extensively illuminating the object surface beyond the field of view of the image pickup apparatus 5. The first illumination device 6 is formed of a set of LEDs that includes multiple LEDs 6a-n (n=1, 2 . . . ) aligned in the direction y, a collimating lens 6b for collimating light from the LEDs, a diffusing element 6c located in the collimated light flux for diffusing light in the direction x, and a cylindrical lens 6d for collecting in one direction the light diffused by the diffusing element 6c on the surface of the object.

Among the LEDs 6a-n (n=1, 2 ...) forming the LED set 6a, an LED corresponding to a point to be measured on the object surface is energized. Light from the LED passes through the collimating lens 6b, is diffused in the direction x by the diffusing element 6c, and forms a light beam that illuminates a linear region L for spectroscopic measurement on the object surface via the cylindrical lens 6d. Each LED of the LED set 6a is individually energized.

Figures 11A, 11B:
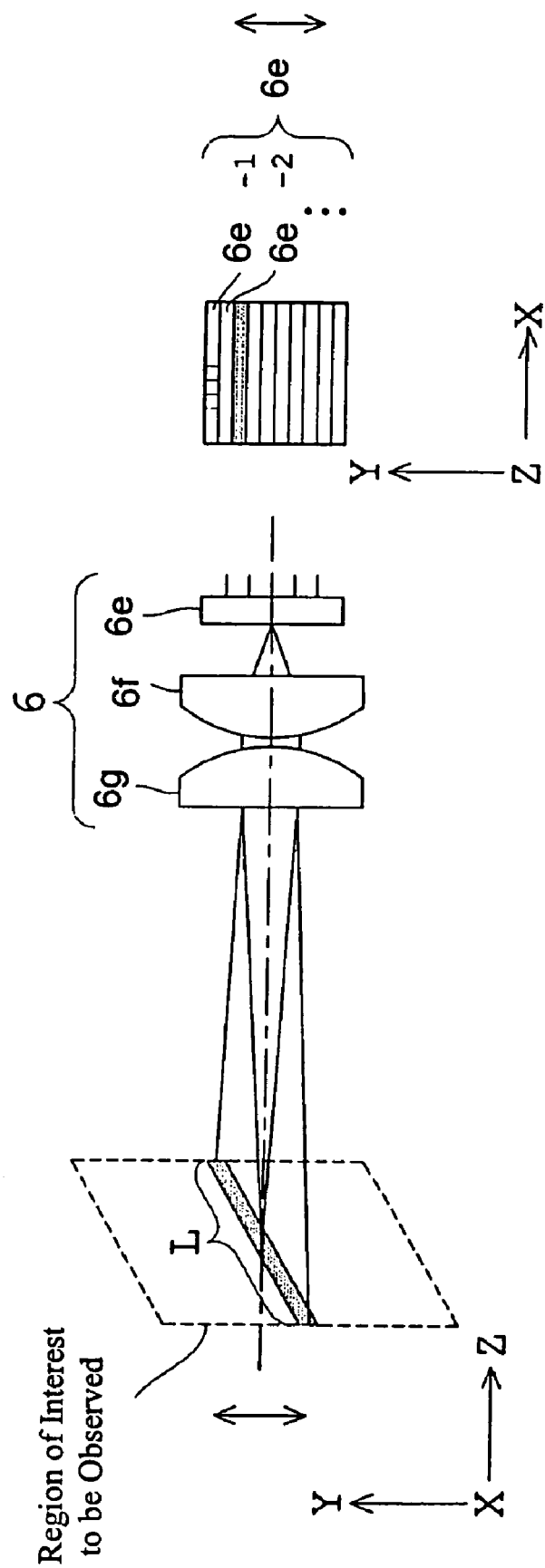
FIGS. 11(a) and 11b) are illustrations showing another possible construction of the illumination device 6, with FIG. 11(a) being a partial cross-section containing the optical axis of the illumination device 6, and FIG. 11(b) being a view along the optical axis showing the arrangement of a set of LEDs 6e.

FIGS. 11(a) and 11(b) are illustrations showing another possible construction of the first illumination device 6, with FIG. 11(a) being a partial cross-section containing the optical axis of the first illumination device 6, and FIG. 11(b) being a view along the optical axis showing the arrangement of a set of LEDs 6e. In FIG. 11(a), the object surface is shown in a perspective view for greater clarity of explanation. In the figure, the first illumination device 6 comprises a set of LEDs 6e formed of multiple LEDs arranged in a two dimensional plane x-y, a collimating lens 6f, and a cylindrical lens 6g. The LED set 6e includes a group of multiple LEDs that are linearly arranged in the direction x and multiple LED groups are arranged in the direction y. Each group of LEDs 6e-n (n=1, 2 ...) in the direction x is individually energized. Light emitted from the LED set 6e is collimated by the collimating lens 6f and enlarged and projected onto the object surface with the linear shape maintained by the cylindrical lens 6g. Thus, the target region L for spectroscopic measurement on the object surface, which is a linear region, is illuminated by linearly shaped illumination light.

With the above construction, the object surface can be scanned in the direction y by illuminating a linear region with the optical axis of the first illumination device 6 being fixed relative to the object surface. It is preferred that a diffusion agent for mixing color lights emitted from the LEDs, an agent that produces fluorescence using the light emitted from the LEDs as an excitation source to produce white light, and an intensity correction filter for homogenizing the light intensity among wavelengths in a desired range be provided in front of the light exit surface of each LED.

The second illumination device 7 is formed of a light guide 7a that guides light from a light source (not illustrated) to the insertion end of an endoscope, and a plano-concave lens 7b that diffuses light emitted from the light guide 7a and illuminates the object surface so that the second illumination device 7 extensively illuminates the object surface beyond the field of view of the image pickup apparatus 5.

The construction of the illumination devices is not limited to those specifically described above. Any illumination device can be used in combination with the image pickup apparatus 5 provided that it illuminates a linear region of the object surface and/or that it extensively illuminates the object surface.

As shown in FIG. 10(b), while the second illumination device 7 extensively illuminates the object, an image of the entire object is obtained in the imaging area of the zero-order light on the image pickup surface of the solid-state image pickup element 4 and, concurrently, spectral images of the entire object are obtained in the imaging area of the −1st-order light on the image pickup surface. On the other hand, as shown in FIG. 10(c), while the first illumination device 6 illuminates a relatively narrow, linear region of the object, an image of the illuminated object is obtained in the imaging area of the zero-order light on the image pickup surface of the solid-state image pickup element 4 and, concurrently, spectral images of the illuminated object part are obtained in the imaging area of the −1st-order light on the image pickup surface.

Figure 12C:
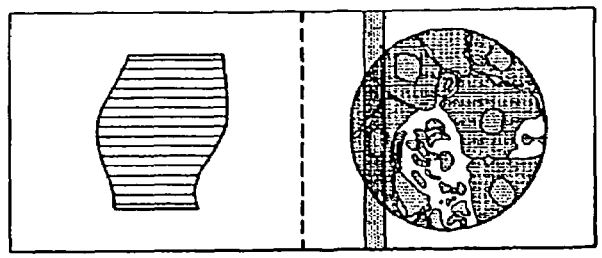
FIGS. 12(a)-12(c) are illustrations to schematically show an image display obtained using the observation system for measuring spectral reflectance according to Embodiment 5 of the present invention.
Figure 12B:
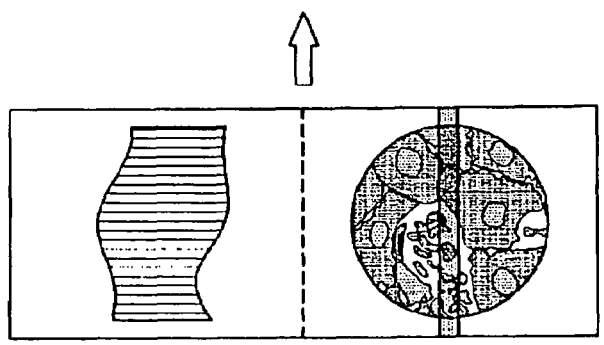
Figure 12A:
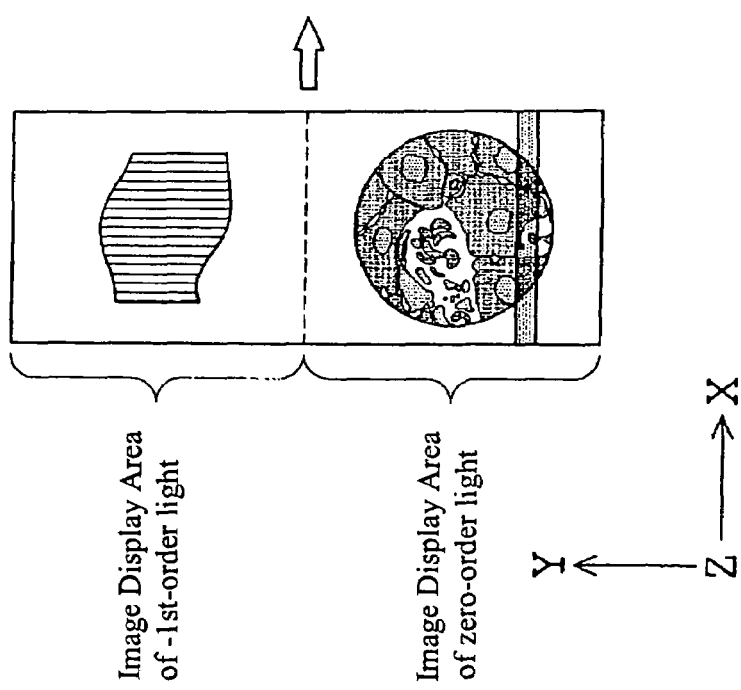

An image processing device and a display device can be used to merge and display images obtained using different illumination devices, as shown in FIGS. 12(a)-12(c) by way of example. In FIG. 12(a), a zero-order light image obtained using the second illumination device 7 is displayed along with lines indicating where the illuminated region L (shown in FIG. 11(a)) is on the object surface, calculated on the basis of the zero-order light image obtained using the second illumination device 7. Above the image formed by the zero-order light, spectral images of the illuminated regions obtained using the first illumination device 6 are shown. The arrangement of these images allows the observer to acquire the morphological information of the object surface and the positional information of the linear illumination region from the images displayed in the lower area, and to acquire the spectral information of the object surface from the images displayed in the upper area. The first illumination device 6 scans the illuminated region L over the object surface and individually obtained spectral images are stored in an image processing device. The image of a specific illuminated region L can be retrieved and displayed. With this construction, the spectral images over the entire object surface can be individually obtained for different wavelength bands as shown in FIGS. 12(a)-12(c). The observer can screen out unnecessary spectral images while viewing these images. Furthermore, the image processing device 54 can serve to extract image information for a specific wavelength among the spectral images of the illuminated regions L and merge extracted image information in order to display an image of the entire object surface.

Figure 13:
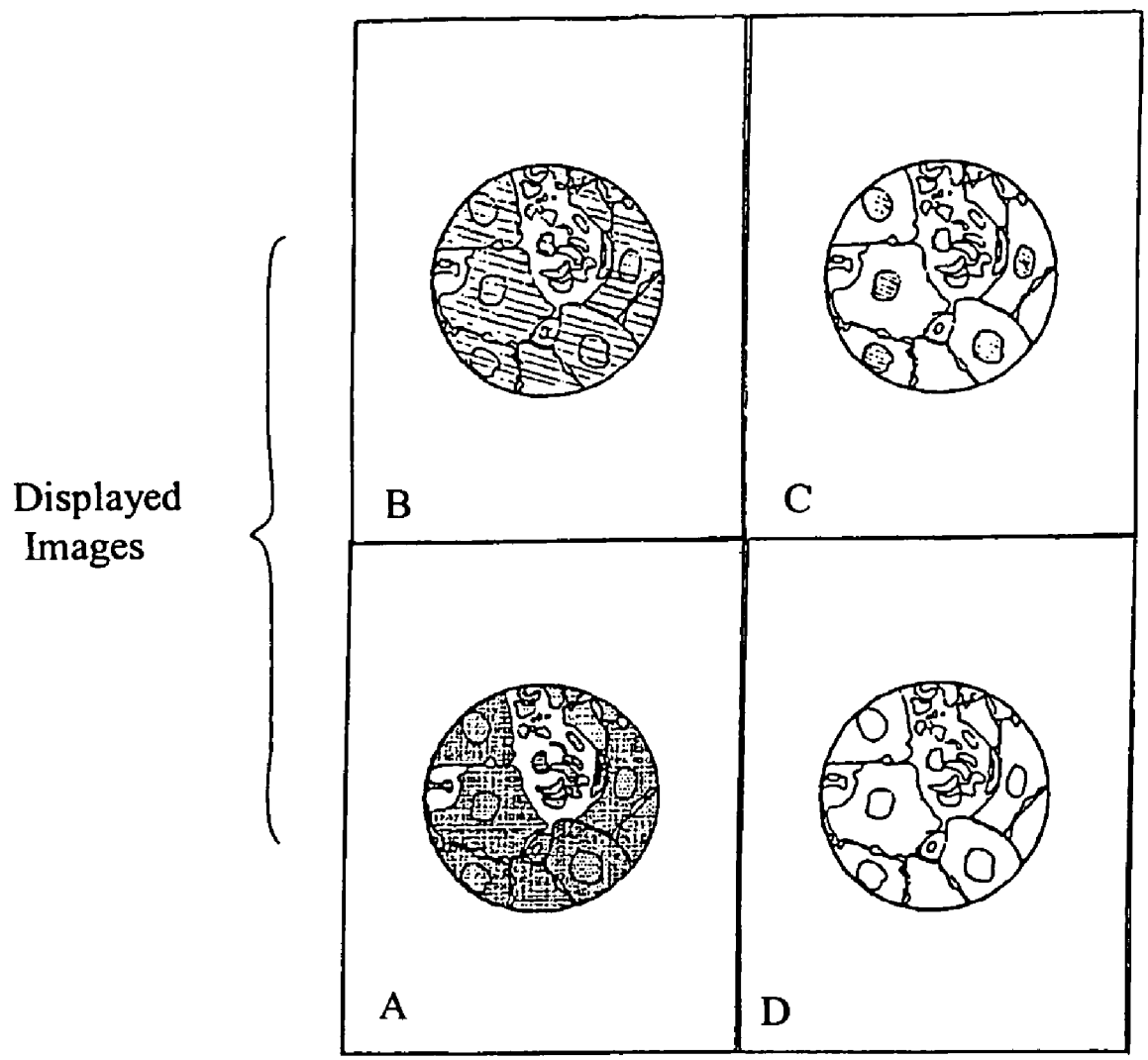
FIG. 13 is an illustration to schematically show another image display obtained using the observation system for measuring spectral reflectance according to Embodiment 5 of the present invention.

FIG. 13 shows object surface images obtained based on individual image information that is displayed on a display screen divided into four sections. The display screen A displays a zero-order light image obtained using the illumination device 7. When the illumination device 7 emits white light, a color image is displayed on the display screen A. The display screen B displays an image based on image information for a specific wavelength. The display screen C displays an image based on image information for another specific wavelength. The display screen D displays a differential image of the image displayed on the display screens B and C.

In this way, images carrying different information can be compared, thereby a specific phenomenon that appears at a specific point on the object surface can be precisely observed and its spectrum viewed.

Embodiment 6

FIGS. 14(a)-14(c) are illustrations to explain the construction of an observation system according to Embodiment 6 for measuring spectral reflectance in which the image pickup apparatus of the present invention is mounted, with FIG. 14(a) schematically showing the various components of the observation system and its construction, with FIG. 14(b) showing an illumination light flux in the illumination device 16 as seen in the direction z, and with FIG. 14(c) showing an illumination light flux in the illumination device 16 as seen in the direction x.

Figure 15B:
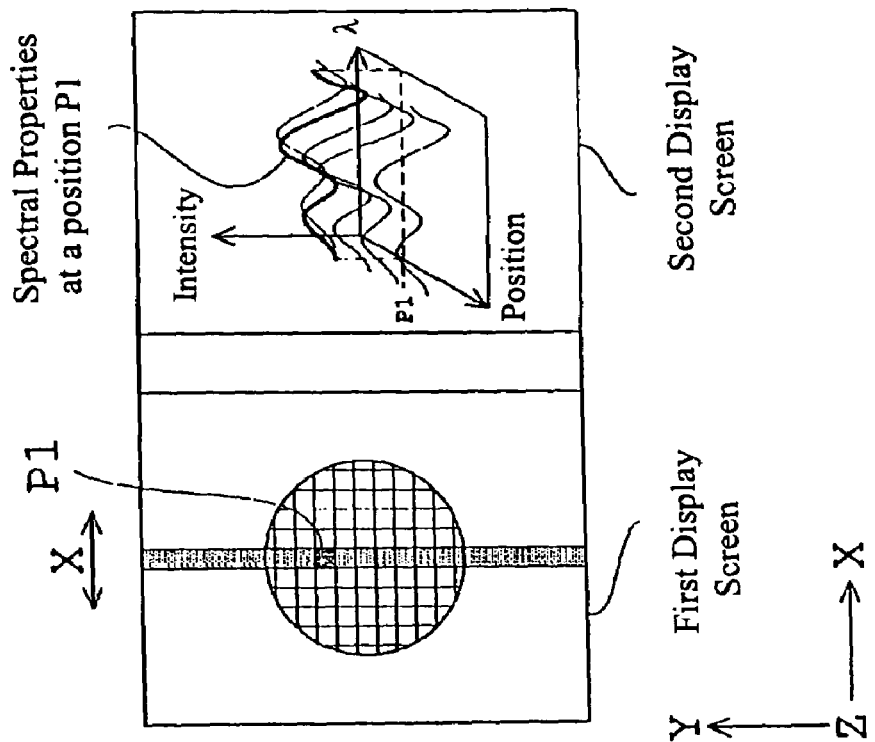
FIGS. 15(a) and 15(b) are illustrations to schematically show an image display obtained using the observation system for measuring spectral reflectance according to Embodiment 6 of the present invention.
Figure 15A:
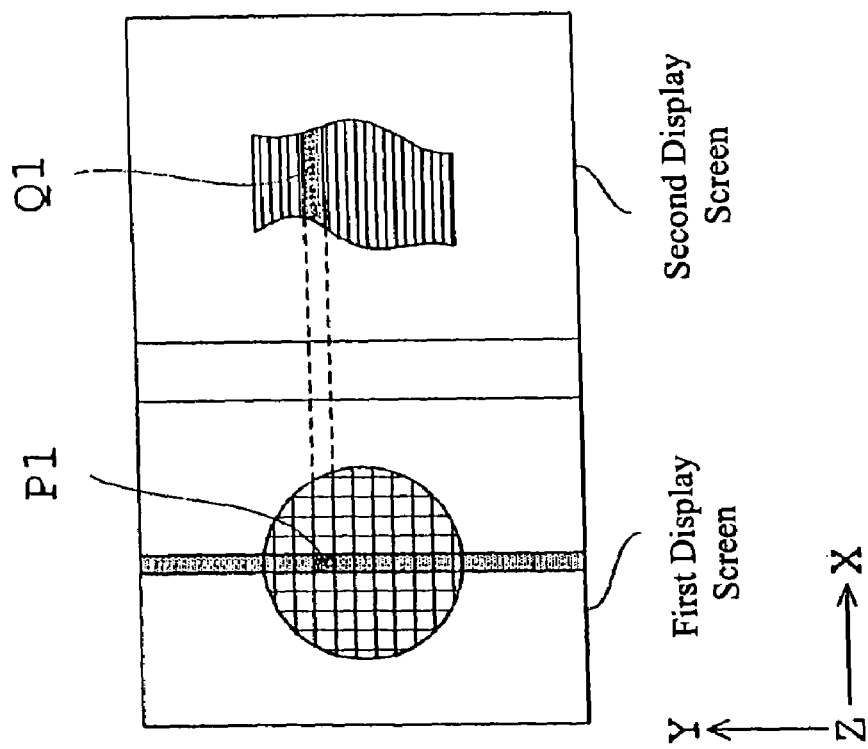

FIGS. 15(a) and 15(b) are illustrations showing information obtained by a light receiving element 14 of the observation system after the information has been processed by an image processing device (not shown), and displayed on display screens.

As shown in FIGS. 14(a)-14(c), the observation system for measuring spectral reflectance in this embodiment is formed of an objective lens 15, a diffraction element 13, an imaging lens 12, a light receiving element 14, an illumination device 16 for illuminating a linear region of an object surface with white light, an illumination device 17 for illuminating the object surface with infrared light, and half mirrors 18 and 19.

The illumination device 16 is formed of a white light source 16a, a collimating lens 16b, and a diffusing element 16c. As shown in FIGS. 14(b) and 14(c), the diffusing element 16c simply transmits light in the direction z and diffuses light in the direction y. The illumination device 17 is formed of an infrared light source 17a, a diffusing element 17b, and a collimating lens 17c. The diffusing element 17b diffuses incident light evenly in the directions x and y.

The observation system for measuring spectral reflectance of this embodiment further includes a stage 20 on which an object is placed and a stage driving mechanism (not shown) for moving the stage in the direction x in the figure, as shown by the double-headed arrows.

In the observation system for measuring spectral reflectance of this embodiment, the illumination device 17 first illuminates the object surface with light in the infrared range. Infrared rays emitted from the infrared light source 17a enter the half mirror 19 as a collimated light flux via the diffusing element 17b and the collimating lens 17c. After being reflected by the half mirror 19 and transmitted through the half mirror 18, the infrared light illuminates the object surface on the stage 20 via the objective lens 15. The infrared light that is reflected by the object surface enters the half mirror 18 as a collimated light flux via the objective lens 15. The infrared light that is transmitted through the half mirrors 18 and 19 is separated into zero-order light and −1st-order light and imaged on the light receiving element 14 via the diffraction element 13 and imaging lens 12. In this manner, an infrared image of the object surface is obtained in the imaging area of the zero-order light on the light receiving surface of the light receiving element 14.

Subsequently, the illumination device 16 illuminates a relatively narrow area of the object surface with white light. White light emitted from the light source 16a enters the diffusing element 16c as a collimated light flux via the collimating lens 16b. Upon entering the diffusing element 16c, the white light is diffused only in the direction y. After being reflected by the half mirror 18, the white light passes through the objective lens 15 and illuminates a linear region of the object surface that is oriented in the direction y in the figure. Light reflected by the object surface enters the half mirror 18 as a collimated light flux via the objective lens 15. After being transmitted through the half mirrors 18 and 19, the light is separated into zero-order light and −1st-order light and imaged onto the light receiving element 14 via the spectroscopic element 13 and imaging lens 12. In this manner, a color image of the illuminated region of the object surface is obtained in the imaging area of the zero-order light on the light receiving surface of the light receiving element 14 and the spectrum of the object surface image is obtained in the imaging area of the −1st-order light on the light receiving surface of the light receiving element 14. The stage 20 on which an object surface is placed can be moved to shift the linearly illuminated region on the object surface, thereby obtaining and storing in the memory of an image processing device (not shown) reflection spectral images for the entire object surface.

An image processing device 54 and a display device 56 (shown in block diagram form in FIG. 5) may be used to display infrared images obtained using the illumination device 17 and the spectral images obtained using the illumination device 16 side-by-side on one or more display screen(s). In addition, the coordinates of the linearly illuminated region on the object surface can be calculated based on the color image obtained using the illumination device 16 and a mark that indicates the illuminated region can be merged with, and appear on, the infrared image. For example, a display may be divided vertically into two parts as shown in FIG. 15(a), so that a first display screen displays an infrared image of the object surface and so that a second display screen displays the spectral content of the visible image. The region of the object that is linearly illuminated with light is marked on the infrared image that is displayed on the first display screen so that it is known from which part of the object surface the spectral images that are displayed on the second display screen are taken. Furthermore, a spectral intensity analysis that focuses on the reflectance spectrum Q1 for a small region P1 within the marked region on the object surface can be provided. FIG. 15(b) shows a spectral intensity profile for the small region P1 that may be displayed on the second display screen. In this way, a specific small region P1 on the object surface is selected and the spectral intensity profile for the region is analyzed.

Embodiment 7

Figure 16:
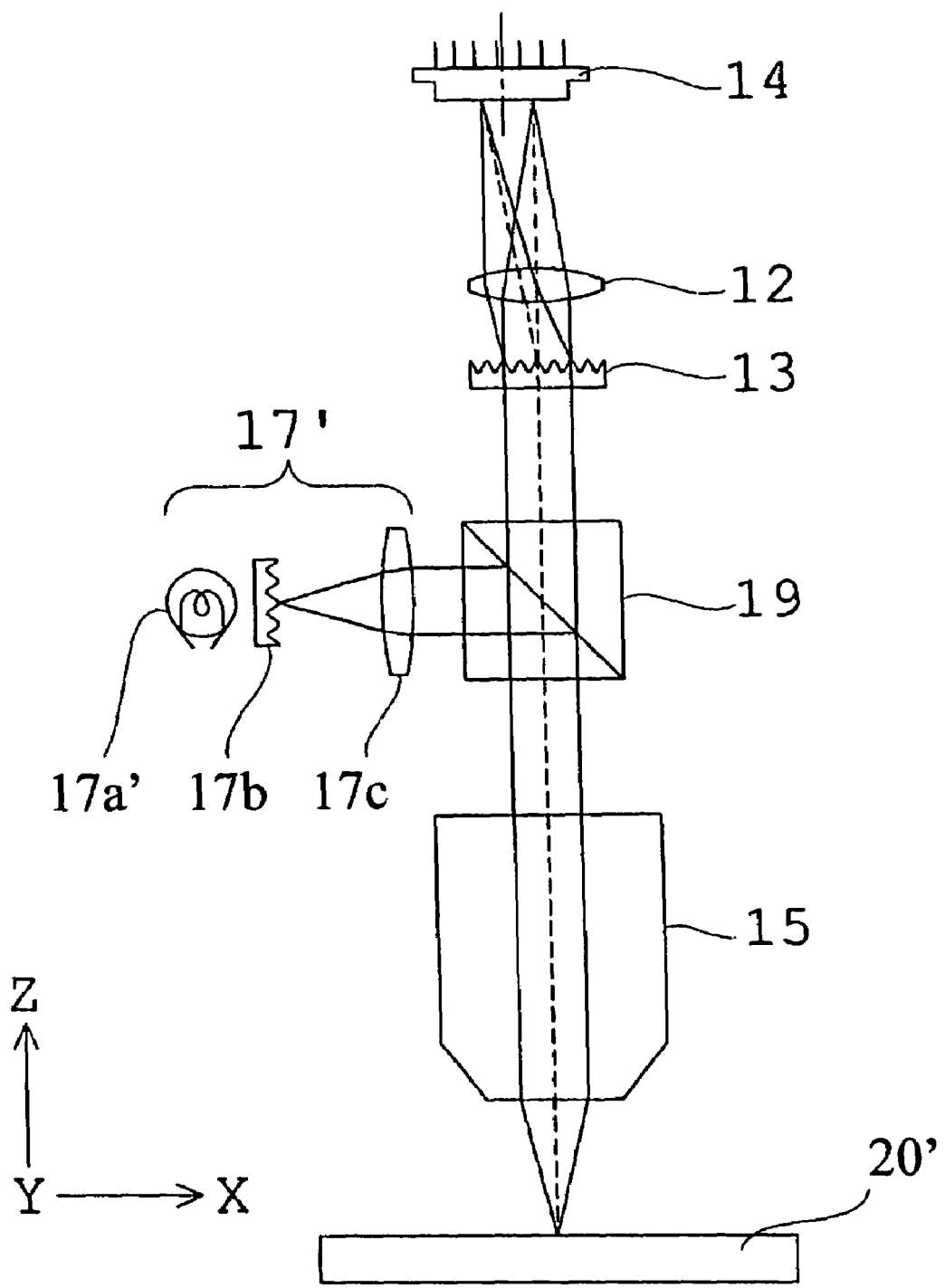
FIG. 16 is an illustration showing the construction of an observation system for inspecting the quality of LEDs according to Embodiment 7 of the present invention.
Figure 17:
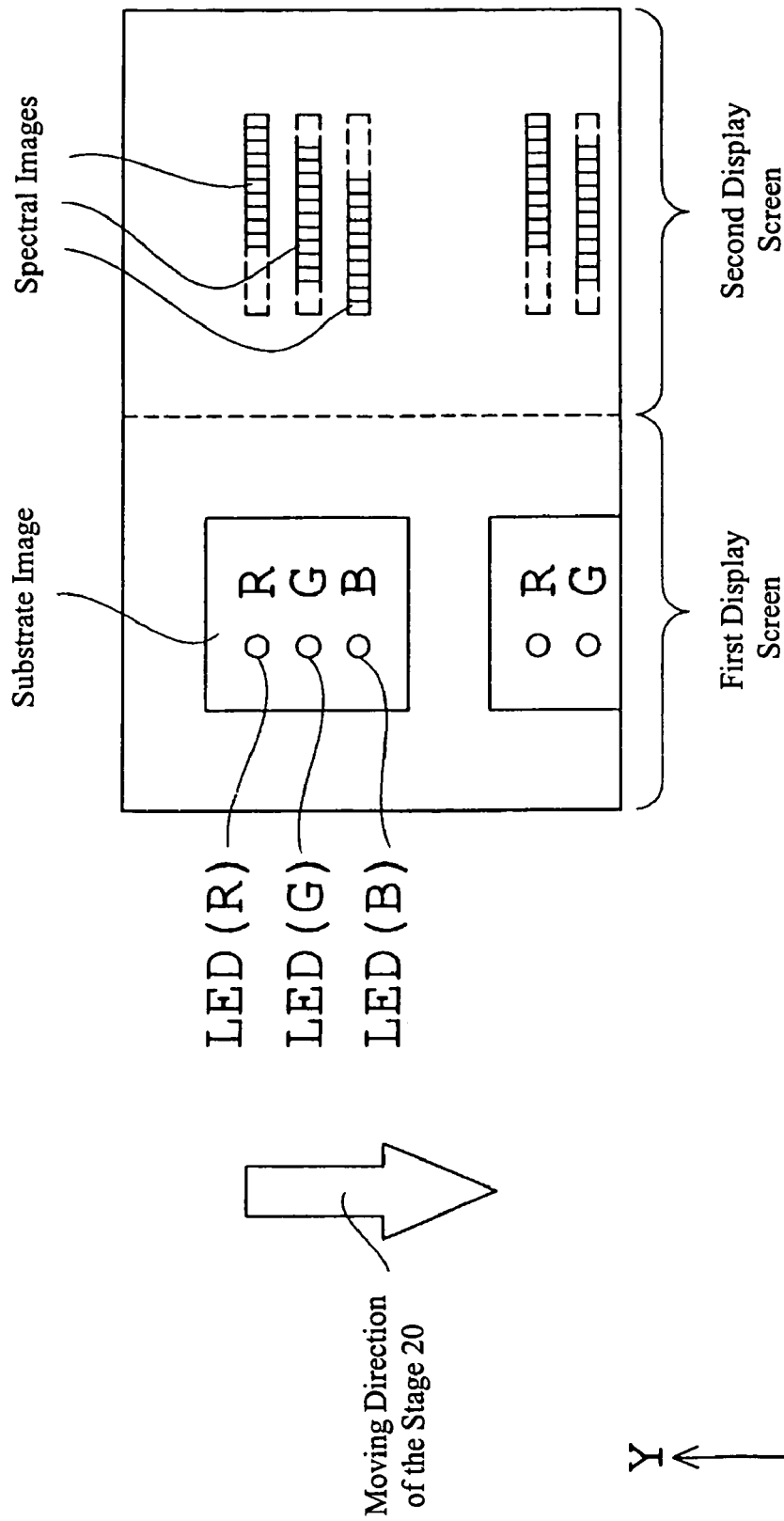
FIG. 17 is an illustration to schematically show an image display obtained using the observation system for inspecting the quality of LEDs according to Embodiment 7 of the present invention.

FIG. 16 is an illustration that schematically shows the construction of an illuminant observation system in which the image pickup apparatus according to Embodiment 7 of the present invention is mounted. FIG. 17 is an illustration that shows information that is obtained by a light receiving element 14 of the illuminant observation system of FIG. 16 after the information has been processed by an image processing device (not shown), and displayed on a display device that includes, for example, a first display screen and a second display screen.

The illuminant observation system of FIG. 16 is formed of an objective lens 15, a spectroscopic element 13, an imaging lens 12, a light receiving element 14, an illumination device 17', and a half mirror 19. An object is placed on a stage 20' and moved by a stage driving mechanism (not shown) in the y direction. As shown in FIG. 16, the illumination device 17' may be formed of a light source 17a' that emits white light, a diffusing element 17b, and a collimating lens 17c. The illumination device 17' has the same construction as the illumination device 17 of Embodiment 6 except the light source 17a' is different in that it emits visible light rather than infrared light. The other optical elements have the same construction in Embodiment 7 as the like-numbered other optical elements in earlier embodiments.

The observation system of the present embodiment is for inspecting illumination light sources, such as LEDs. The stage 20' is elongated in the direction y in the figure. Multiple substrates having red, green, and blue LEDs are arranged on the stage 20' in the direction y. The LEDs are energized for inspection. The illumination device 17' intermittently emits white light. For example, the illumination device 17' can be a flash lamp. While the illumination device 17' is energized, light from the illumination device 17' enters the half mirror 19 as a collimated light flux via the diffusing element 17b and the collimating lens 17c. After being reflected by the half mirror 19, the light extensively illuminates the object surface on the stage 20' via the objective lens 15. Light reflected by the object surface enters the half mirror 19 as a collimated light flux via the objective lens 15. The light transmitted through the half mirror 19 is separated into zero-order light and −1st-order light and is imaged on the light receiving element 14 via the spectroscopic element 13 and the imaging lens 12. In this manner, a color object surface image is obtained in the imaging area of the zero-order light on the light receiving surface of the light receiving element 14.

While the illumination device 17' is off, light from the LEDs (not shown in FIG. 16) enters the half mirror 19 as collimated light fluxes via the objective lens 15. The light transmitted through the half mirror 19 is separated into zero-order light and −1st-order light and is imaged onto the light receiving element 14 via the spectroscopic element 13 and the imaging lens 12. Then, spectral images for the LEDs are obtained in the imaging areas of the −1st-order light on the light receiving surface of the light receiving element 14.

The stage 20 may be moved in accordance with the illumination cycle of the illumination device 17' so that the inspection of LEDs may be continuously performed. Images that are obtained may be stored in an image processing device (not shown in FIG. 16).

The image processing device and the display device may display, side-by-side on a display screen or screens: color object surface images obtained while the illumination device 17' is energized; and spectral images obtained while the illumination device 17' is not energized. For example, as illustrated in FIG. 17, the display may be divided vertically into two parts. A first display screen displays color object surface images and the second display screen displays spectral images of the LEDs. The substrate on which the LEDs are mounted and the LEDs may be inspected by viewing color images on the first display screen. Furthermore, the LEDs can be checked for quality by viewing spectral images of the LEDs on the second display screen and comparing each LED output with reference LED spectral data.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An observation system comprising:
    an image pickup apparatus which includes:
        an observation optical system that forms an image of an object at an image surface;
        a diffraction optical element that is arranged in the observation optical system and generates zero-order diffracted light, at least one of −1st-order diffracted light and +1st-order diffracted light from light incident onto the diffraction optical element; and
        a solid-state image pickup device arranged at the image surface and that captures two images formed by the observation optical system, namely, an image formed using the zero-order diffracted light and an image formed using one of the −1st-order diffracted light and the +1st-order diffracted light;
    an image processing apparatus that processes information of the images captured by the solid-state image pickup device;
    a display apparatus that displays images supplied by the image processing apparatus;
    a first illumination device for illuminating a relatively narrow area of the object; and
    a second illumination device for illuminating a relatively broad area of the object; wherein
    the image processing apparatus forms an image of the object by using information captured by the solid-state image pickup device using the zero-order diffracted light, and also forms a spectral image of the object by using information captured by the solid-state image pickup device using one of the −1st-order diffracted light and the +1st-order diffracted light; and
    the image processing apparatus extracts spectral information of the object from one of the −1st-order diffracted light image and the +1st-order diffracted light image captured by the solid-state image pickup device when the object is illuminated by the first illumination device, and extracts morphological information of the object from the zero-order diffracted light image captured by the solid-state image pickup device when the object is illuminated by the second illumination device.

2. The observation system according to claim 1, wherein the image processing apparatus further comprises a memory for storing the image data and the spectral image data, and supplies a composite image to the display apparatus using the stored image data and spectral image data.

3. The observation system according to claim 1, wherein the image processing apparatus forms one image by extracting a specific wavelength information from a plurality of images that include spectral information captured when the object is illuminated by the first illumination device.

4. The observation system according to claim 1, wherein the first illumination device is adapted to scan an area on the object.

5. The observation system according to claim 1, wherein the first illumination device includes an LED.

* * * * *